US005739025A

United States Patent [19]
Fukazawa

[11] Patent Number: 5,739,025
[45] Date of Patent: Apr. 14, 1998

[54] METHOD FOR PRODUCING AN ASPARAGINYL ENDOPROTEASE

[75] Inventor: Chikafusa Fukazawa, Tsukuba, Japan

[73] Assignee: Director of National Food Research Institute, Ministry of Agriculture, Forestry and Fisheries, Tsukuba, Japan

[21] Appl. No.: 486,721

[22] Filed: Jun. 7, 1995

Related U.S. Application Data

[62] Division of Ser. No. 91,991, Jul. 12, 1993, abandoned.

[30] Foreign Application Priority Data

Jul. 22, 1992 [JP] Japan .................................. 4-215739

[51] Int. Cl.[6] ...................................................... C12N 9/50
[52] U.S. Cl. ........................ 435/219; 435/814; 435/815
[58] Field of Search ................................. 435/219, 814, 435/815

[56] References Cited

FOREIGN PATENT DOCUMENTS 429 162  5/1991  European Pat. Off. .

OTHER PUBLICATIONS

Shutov et al. (1982) *Biokhimiya*, 47(5), "Purification and Partial Characterization of Protease B from Germinating Vetch Seeds", pp. 814–822.

Matsushita et al. (1991) *Tanpankushitsu Kakusan Koso (Prot. Nucl. Acid Enzym.)*, 36(4), "Asparaginylendopeptidase", pp. 730–736 (English translation is provided. Japanese is in parent application).

Pesce et al. (1967) *J. Biol. Chem.*, 242(9), "The Comparative Enzymology of Lactic Dehydrogenase", pp. 2151–2167.

Shin–ichi Ishii et al, "An Asparaginyl Endopeptidase Purified from Jackbean Seeds", vol. 9, pp. 294–295, (1990), *J. Protein Chem.*

Ikuko Hara Nishimura et al, "A Unique Vacuolar Processing Enzyme Responsible for Conversion of Several Proprotein Precursors into the Mature Forms", vol. 294, No. 1, 2, pp. 89–93, (1991) *Febs Letters.*

M. Scott et al, "A Protease Responsible for Post–Translational Cleavage of a Conserved Asn–Gly Linkage in Glycinin, the Major Seed Storage Protein of Soybean", vol. 89, pp. 658–662, (1992) *Proc. Natl. Acad. Sci. USA.*

*Primary Examiner*—Jon P. Weber
*Attorney, Agent, or Firm*—Frishauf, Holtz, Goodman, Langer & Chick, P.C.

[57] ABSTRACT

A method is provided for preparing an asparaginyl endoproteinase from the seeds of soybean, ginkgo and rice which have been collected between an early growing stage and ripening. The method comprises the steps of dialyzing an extract of the seeds against an acidic buffer of pH 4.0 to 6.0, ammonium sulfate precipitation, hydrophobic chromatography and gel filtration. The resulting asparaginyl endoproteinase cleaves glycinin between the C-terminal amino acid residue of the acidic subunit region, Asn, and the N-terminal amino acid residue of the basic subunit region, Gly or Asn.

10 Claims, 17 Drawing Sheets

FIG. 6A

```
pOGT817      ----------------------------------------ACCATTCCACCTTCTACAATCTTTCAAACAATCATG
pOGT664                                                                              Met

*    *    *    *    *    *    *    *    *    *    *    *    *    *    * pOGT817      ------------------------------------------------------------------------
pOGT664      GCAACTACTAGTTTTCCATCGGTATTGTTTACTCTTGCATTTTCTTATACAATGATCATGCT
             AlaThrSerPheProSerValLeuPheTyrSerCysIlePheLeuLeuTyrAsnGlySerMetAla

*    *    *    *    *    *    *    *    *    *    *    *    *    *    * pOGT817      ------------------------------------------------------------------------
pOGT664      CAACTATTCGGACAGAGCTTTACTCCAAGCTCCGACAAGGAGTTTAAAGGGTGCAAATTT
             GlnLeuPheGlySerPheThrProTrpGlnSerSerArgGlnGlyGlyLeuLysGlyCysLysPhe
                                                                              *

*    *    *    *    *    *    *    *    *    *    *    *    *    *    * pOGT817      ------------------------------------------------------------------------
pOGT664      GATAGGCTGCAAGCATTTGAACGGCTTCGACAAGTGAGGCGGTGTCACAAGCGGGTGTACTCGAGTACTTGAT
             AspArgLeuGlnAlaPheGluProLeuArgSerGlnValArgArgCysHisLysArgValThrGluTyrPheAsp

*    *    *    *    *    *    *    *    *    *  | Ser |  *    *    *    *
                                                             |  CT |
pOGT817      --G-----------------------------A--------C--G-----|-----|----T-----C-------
pOGT664      GAACAGAATGAGCAATTCGTTGTACTGGTGTGTTCGTCATTCGTCGTGTTATCGAGCCTCAAGGCCTC
             GluGlnAsnGluGlnPheValValLeuArgCysThrGlyValPheArgCys|ValIle|ArgArgValIleGluProGlnGlyLeu
                                         | Leu |
                                         |  A  |
```

FIG. 6B

```
                                                                                                    92
pOGT817  *********-T-------*********C--A--C-TC**********--------****************************-T-------
pOGT664  CTGTTACCTCAATACCACAATGCTCCTGATTGTGTAGATCTTCAAGTAGGGATACACAGGGTTG
         LeuLeuProGlnTyrHisAsnAlaProGlyLeuValTyrIleLeuGlnGlyArgGlyTyrThrGlyLeu

Leu             Ala                    Val                           Phe
pOGT817  *******-------*********A--T----*********G--**********-------*********C--T-**********-----T---T--G
pOGT664  ACTTTCCGGATGCCACAACCTTCCAACAGTTCCAACCATTTGATCCACAGTTTGATGTTATTGCTGCCA
         ThrPheProGlyCysProAlaThrPheGlnGlnPheGlnProPheAspValIleAlaAlaPro

138
                                                                             Arg         Gly
pOGT817  *********************************************-----G-*******-G-------
pOGT664  CAAAGCCATTCAAAGATGAGCACCAAGAGTTCACCGCCTTAAACAAGACGTTTAAGGAGATGTTATTGGCTGCCA
         GlnSerHisLeuLysAspGluHisGlnArgPheLysGlnArgValHisGlnLysAspValPheLysGluMetLeuLeuAlaAla 184
pOGT817  --T-------------------------------A-----------------------
pOGT664  GCCGGCATTGTACACTGGGCTACAATGATGGTAGCTCCGGTTGAGCTATCTATGTCTTCGACGTA
         AlaGlyIleValHisTrpGlyTyrAsnAspValAlaProValAlaAlaIleTyrValPheAspVal pOGT817  *************************************************
pOGT664  AACAACAACGCTAATCAACTGAACCTAGACAAAGGAGTCTGTTGGCTGTAACAATAAGGAAGAT
         AsnAsnAsnAlaAsnGlnLeuAsnLeuAspLysGlyValCysTrpLeuAsnAsnLysGluAsp
```

FIG.6C

```
pOGT817    ------------------------------------------------
pOGT664    CAACAATTTGGACAAAACATATTCAGCGGATTCAATATCCAACTTCTTAGTGAGGCTCTTGGTATAAGT
           GlnGlnPheGlyGlnAsnIlePheSerGlyPheAsnIleGlnLeuLeuSerGluAlaLeuGlyIleSer
                                                                              230 pOGT817    ------------------------------------------------
pOGT664    CAACAAGCAGCACAGAGGATCCAAAGTCAAATCAACAAAGAAGAGTGAGATAATTCGTGTGACTCAACGC
           GlnGlnAlaAlaGlnArgIleGlnSerGlnIleGlnGlnArgArgValIleIleArgValThrGlnArg pOGT817    -----------A------------------------------------
pOGT664    CTTCAATTCTTGAAGCCAACAATGTCCCAACAAGAACATCAAGCCTACCAAGCATCAACCAACCAATTCAA
           LeuGlnPheLeuLysProThrMetSerGlnGlnGluHisGlnAlaTyrGlnAlaTyrGlnProIleGln pOGT817    -----------------------------------.--#-#-#-#-#--
pOGT664    AGTCAAGAAGGACAATCAACCCAATACCAGTAGGCAATCAACCCAATATCAAGAAGACAATCAACT
           SerGlnGluGlyGlnSerThrGlnTyrGlnValGlyGlnSerThrGlnTyrGlnGluGlyGlnSerThr
                                                                              276
```

FIG. 6D

```
pOGT817  ............................................................
pOGT664  CAATACCAGGCAGGACAGGAGTCACAGACAGTTCAATGGTTGGAGGAGAACTTTGTCATTGGAG
         GlnTyrGlnAlaGlyGlnSerGlnAspArgSerPheAsnGlyLeuGluGluAsnPheCysSerLeuGlu pOGT817  ..........[Lys].............[Glu]..........................  322
                  [ A ]             [ A ]
pOGT664  GCAAGGCAGAACATGGAATCGGAACCCAAGTGCCGACACGCAACCCAGTGCTGTAGGAAACACGT
         AlaArgGlnAsnIleGlyAsnProLysArgAlaAspThrHisAsnProArgAlaGlyArgIleThrArg
                                                  * *                [Tyr]
                                                                     [ T ]

pOGT817  ....................A.......................................
pOGT664  CTCCATGGCCAGAATTCCCATCCTTAACCTGTGCAAATGAGGCCACAAGAGTAATCTATACCAG
         LeuHisGlyGlnAsnPheProIleLeuAsnLeuValGlnMetSerAlaThrArgValAsnLeuTyrGln pOGT817  ....................................T.......................  368
pOGT664  AATGCTATTCTTTCACCATTCTGGAACATCAATGCACAGTGGTCTACATGATCCAAGGCATGCT
         AsnAlaIleLeuSerProPheTrpAsnIleAsnAlaHisSerValValTyrMetIleGlnGlyHisAla
```

```
pOGT817  ----------------------------------------
pOGT664  TCTGGTGTATTCACTCCAAATTACCCAAACGAGCTTCCAACCTTATCCAGAGGGCAGGATGAGTCA
         SerGlyValPheThrProLysThrThrSerPheGlnThrProTyrProGluGlyAlaAspGluSer pOGT817  ----------------[Ile]--------G---AGG---C-A---------------------- 491
pOGT664  TCTTTCACTACTAATAAGG CAT AATCAGAGTAAATTAGTGAGTGTAATGGAACTAGTAGTATAGTGAAATAAAGCA
                         [ T ]
         SerLeuThrAsnLysAlaSerGlu*** pOGT817  ------------------------------------------------------------ -poly(A)
pOGT664  TCGCAAGTGTGGAAGTGGGTGGTATATAACCGCTTATCTTAATAAATAACTTCATCATGTT -poly(A)
```

FIG. 6G

☐, changed amino acid residues; *, identical residues; ●, similar amino acid residues; #, deleted amino acid residues; ▬, repeated sequence; ▼, post-translational cleavage site; ✱, N-terminus of acidic subunit region; ✱✱, N-terminus of basic subunit region FIG.8A
FIG.8B
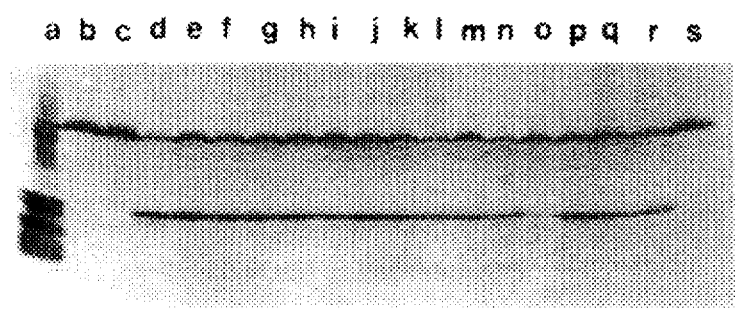
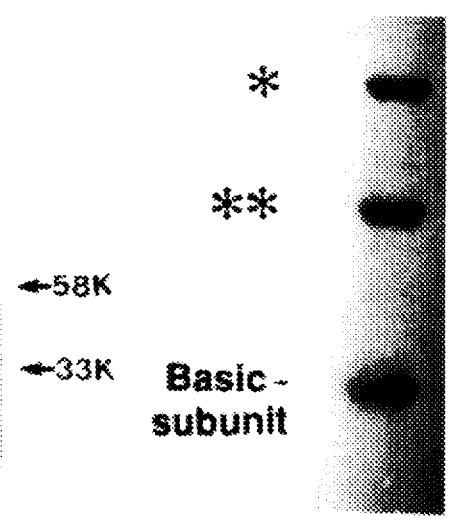

(A)

(B)

Retention time (min)

SEQUENCE LISTING ( 1 ) GENERAL INFORMATION:

( i i i ) NUMBER OF SEQUENCES: 22

( 2 ) INFORMATION FOR SEQ ID NO:1:

( i ) SEQUENCE CHARACTERISTICS:
        ( A ) LENGTH: 1685 base pairs
        ( B ) TYPE: nucleic acid
        ( C ) STRANDEDNESS: double
        ( D ) TOPOLOGY: linear ( i i ) MOLECULE TYPE:c-DNA ( i i i ) HYPOTHETICAL:

( i v ) ANTI-SENSE:

( v ) FRAGMENT TYPE:

( v i ) ORIGINAL SOURCE:
        ( A ) ORGANISM: Oat (Avena sativa, L.)
        ( B ) STRAIN:
        ( C ) INDIVIDUAL ISOLATE:
        ( D ) DEVELOPMENTAL STAGE: middle stage
        ( E ) HAPLOTYPE: 2n
        ( F ) TISSUE TYPE:
        ( G ) CELL TYPE:
        ( H ) CELL LINE:
        ( I ) ORGANELLE: cotyledon ( v i i ) IMMEDIATE SOURCE:
        ( A ) LIBRARY: cDNA library
        ( B ) CLONE: A2B ( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY: Oat 12S globulin / 11- S protein Family
        ( B ) LOCATION: protein bodies of cotyledonary tissue
        ( C ) IDENTIFICATION METHOD:
        ( D ) OTHER INFORMATION:

( x ) PUBLICATION INFORMATION:
        ( A ) AUTHORS:
        ( B ) TITLE:
        ( C ) JOURNAL:

( x i ) SEQUENCE DESCRIPTION: SEQ ID NO:1:

```
ACCATTCCAC CTTCTACAAT CTTTTCAAAC AATC ATG GCA ACT ACT AGT TTT CCA      55
                                     Met Ala Thr Thr Ser Phe Pro
                                                     -20

TCG GTA TTG TTT TAC TCT TGC ATT TTT CTC TTA TAC AAT GGA TCC ATG       103
Ser Val Leu Phe Tyr Ser Cys Ile Phe Leu Leu Tyr Asn Gly Ser Met
        -15              -10                      -5

GCT CAA CTA TTC GGA CAG AGC TTT ACT CCA TGG CAA AGC TCT CGA CAA       151
Ala Gln Leu Phe Gly Gln Ser Phe Thr Pro Trp Gln Ser Ser Arg Gln
     1           5                   10                      15

GGA GGT TTA AAG GGG TGC AAA TTT GAT AGG CTG CAA GCA TTT GAA CCG       199
Gly Gly Leu Lys Gly Cys Lys Phe Asp Arg Leu Gln Ala Phe Glu Pro
             20              25                      30

CTT CGA CAA GTG AGG TCA CAA GCG GGT GTC ACT GAG TAC TTT GAT GAA       247
Leu Arg Gln Val Arg Ser Gln Ala Gly Val Thr Glu Tyr Phe Asp Glu
                 35              40                      45

CAG AAT GAG CAA TTT CGT TGT ACT GGT GTA TTC GTC ATT CGT CGT GTT       295
Gln Asn Glu Gln Phe Arg Cys Thr Gly Val Phe Val Ile Arg Arg Val
             50                  55                  60
```

```
ATC GAG CCT CAA GGC CTC CTG TTA CCT CAA TAC CAC AAT GCT CCT GGA    343
Ile Glu Pro Gln Gly Leu Leu Leu Pro Gln Tyr His Asn Ala Pro Gly
     65                  70                  75

TTG GTG TAC ATC CTT CAA GGT AGG GGA TAC ACA GGG TTG ACT TTC CCG    391
Leu Val Tyr Ile Leu Gln Gly Arg Gly Tyr Thr Gly Leu Thr Phe Pro
 80                  85                  90                  95

GGA TGC CCA GCA ACC TTC CAA CAA CAG TTC CAA CCA TTT GAT CAA GCC    439
Gly Cys Pro Ala Thr Phe Gln Gln Gln Phe Gln Pro Phe Asp Gln Ala
                100                 105                 110

CAG GAT CAA AGC CAA AGC CAT CTC AAA GAT GAG CAC CAA AGA GTT CAC    487
Gln Asp Gln Ser Gln Ser His Leu Lys Asp Glu His Gln Arg Val His
            115                 120                 125

CGC TTT AAA CAA GGA GAT GTT ATT GCG CTG CCA GCC GGC ATT GTA CAC    535
Arg Phe Lys Gln Gly Asp Val Ile Ala Leu Pro Ala Gly Ile Val His
        130                 135                 140

TGG GGC TAC AAT GAT GGT GAT GCT CCG GTT GTA GCT ATC TAT GTC TTC    583
Trp Gly Tyr Asn Asp Gly Asp Ala Pro Val Val Ala Ile Tyr Val Phe
    145                 150                 155

GAC GTA AAC AAC ACC GCT AAT CAA CTT GAA CCT AGA CAA AAG GAG TTC    631
Asp Val Asn Asn Thr Ala Asn Gln Leu Glu Pro Arg Gln Lys Glu Phe
160                 165                 170                 175

TTG TTG GCT GGT AAC AAT AAG GAA GAT CAA CAA TTT GGA CAA AAC ATA    679
Leu Leu Ala Gly Asn Asn Lys Glu Asp Gln Gln Phe Gly Gln Asn Ile
                180                 185                 190

TTC AGC GGA TTC AAT ATC CAA CTT CTT AGT GAG GCT CTT GGT ATA AGT    727
Phe Ser Gly Phe Asn Ile Gln Leu Leu Ser Glu Ala Leu Gly Ile Ser
            195                 200                 205

CAA CAA GCA GCA CAG AGG ATC CAA AGT CAA AAG GAA CAA AGA GGT GAG    775
Gln Gln Ala Ala Gln Arg Ile Gln Ser Gln Lys Glu Gln Arg Gly Glu
        210                 215                 220

ATA ATT CGT GTG ACT CAA CGC CTT CAA TTC TTG AAG CCA ACA ATG TCC    823
Ile Ile Arg Val Thr Gln Arg Leu Gln Phe Leu Lys Pro Thr Met Ser
    225                 230                 235

CAA CAA GAA CTA GTA GAG CAT CAA GCC TAC CAA CCA ATT CAA AGT CAA    871
Gln Gln Glu Leu Val Glu His Gln Ala Tyr Gln Pro Ile Gln Ser Gln
240                 245                 250                 255

GAA GGA CAA TCA ACC CAA TAC CAG GTA GGG CAA TCA ACC CAA TAT CAA    919
Glu Gly Gln Ser Thr Gln Tyr Gln Val Gly Gln Ser Thr Gln Tyr Gln
                260                 265                 270

GAA GGA CAA TCT ACT CAA TAC CAG GCA GGA CAG TCA CAA GAC AGA AGT    967
Glu Gly Gln Ser Thr Gln Tyr Gln Ala Gly Gln Ser Gln Asp Arg Ser
            275                 280                 285

TTC AAT GGT TTG GAG GAG AAC TTT TGT TCA TTG GAG GCA AGG CAG AAC   1015
Phe Asn Gly Leu Glu Glu Asn Phe Cys Ser Leu Glu Ala Arg Gln Asn
        290                 295                 300

ATC GGA AAC CCC AAA CGT GCC GAC ACG CAC AAC CCA CGT GCT GGT AGG   1063
Ile Gly Asn Pro Lys Arg Ala Asp Thr His Asn Pro Arg Ala Gly Arg
    305                 310                 315

ATA ACA CGT CTC CAT GGC CAG AAT TTC CCC ATC CTT AAC CTC GTG CAA   1111
Ile Thr Arg Leu His Gly Gln Asn Phe Pro Ile Leu Asn Leu Val Gln
320                 325                 330                 335

ATG AGC GCC ACA AGA GTA AAT CTA TAC CAG AAT GCT ATT CTT TCA CCA   1159
Met Ser Ala Thr Arg Val Asn Leu Tyr Gln Asn Ala Ile Leu Ser Pro
                340                 345                 350

TTC TGG ATC ATC AAT GCA CAC AGT GTG GTC TAC ATG ATC CAA GGG CAT   1207
Phe Trp Ile Ile Asn Ala His Ser Val Val Tyr Met Ile Gln Gly His
            355                 360                 365

GCT CAA GTT CAA GTT GTC AAT AAC AAT GGT CAG ACT GTA TTC AAT GAC   1255
Ala Gln Val Gln Val Val Asn Asn Asn Gly Gln Thr Val Phe Asn Asp
        370                 375                 380
```

-continued

| | | | | | | | | | | | | | | | | |
|---|---|---|---|---|---|---|---|---|---|---|---|---|---|---|---|---|
| CGT | CTT | CGC | CAA | GGT | CAG | TTG | CTA | ATC | GTA | CCA | CAA | CAC | TAC | GTT | GTT | 1303 |
| Arg | Leu | Arg | Gln | Gly | Gln | Leu | Leu | Ile | Val | Pro | Gln | His | Tyr | Val | Val | |
| | 385 | | | | 390 | | | | | | 395 | | | | | |
| CTC | AAG | GCG | GCG | GAG | CGT | GAA | GGA | TGC | CAG | TAT | ATC | TCA | TTC | AAG | ACC | 1351 |
| Leu | Lys | Lys | Ala | Glu | Arg | Glu | Gly | Cys | Gln | Tyr | Ile | Ser | Phe | Lys | Thr | |
| 400 | | | | | 405 | | | | | 410 | | | | | 415 | |
| AAC | CCA | AAC | TCC | ATC | GTT | AGC | CAC | ATC | GCT | GGA | AAG | AGC | TCC | ATT | CTT | 1399 |
| Asn | Pro | Asn | Ser | Met | Val | Ser | His | Ile | Ala | Gly | Lys | Ser | Ser | Ile | Leu | |
| | | | | 420 | | | | | 425 | | | | | 430 | | |
| CGT | GCC | TYG | CCC | GTG | GAT | GTC | CTC | GCC | AAT | GCA | TAC | CGC | ATT | TCC | AGG | 1447 |
| Arg | Ala | Leu | Pro | Val | Asp | Val | Leu | Ala | Asn | Ala | Tyr | Arg | Ile | Ser | Arg | |
| | | | 435 | | | | | 440 | | | | | 445 | | | |
| CAA | GAA | GCC | CGA | AAC | CTC | AAA | AAC | AAC | AGG | GGA | CAA | GAG | TCT | GGT | GTA | 1495 |
| Gln | Glu | Ala | Arg | Asn | Leu | Lys | Asn | Asn | Arg | Gly | Gln | Glu | Ser | Gly | Val | |
| | | 450 | | | | | 455 | | | | | 460 | | | | |
| TTC | ACT | CCA | AAA | TTT | ACC | CAA | ACG | AGC | TTC | CAA | CCT | TAT | CCA | GAG | GGC | 1543 |
| Phe | Thr | Pro | Lys | Phe | Thr | Gln | Thr | Ser | Phe | Gln | Pro | Tyr | Pro | Glu | Gly | |
| | 465 | | | | | 470 | | | | | 475 | | | | | |
| GAG | GAT | GAG | TCA | TCT | TTG | ACT | AAT | AAG | GCA | TCA | GAG | TAAATTAGTG | | | | 1589 |
| Glu | Asp | Glu | Ser | Ser | Leu | Thr | Asn | Lys | Ala | Ser | Glu | | | | | |
| 480 | | | | | 485 | | | | | 490 | | | | | | |

AGTGTAATGG AAACTAGTAT AGTGAAATAA AAGCATCGCA AGTGTGGAAG TGGGTGGTAT　　1649

ATAACCGCTT ATCTTAATAA ATAACTTCAT CATGTT　　1685

( 2 ) INFORMATION FOR SEQ ID NO:2:

( i ) SEQUENCE CHARACTERISTICS:
        ( A ) LENGTH: 1556 base pairs
        ( B ) TYPE: nucleic acid
        ( C ) STRANDEDNESS: double
        ( D ) TOPOLOGY: linear ( i i ) MOLECULE TYPE: c-DNA ( i i i ) HYPOTHETICAL:

( i v ) ANTI-SENSE:

( v ) FRAGMENT TYPE:

( v i ) ORIGINAL SOURCE:
        ( A ) ORGANISM: Oat (Avena sativa, L.)
        ( B ) STRAIN:
        ( C ) INDIVIDUAL ISOLATE:
        ( D ) DEVELOPMENTAL STAGE: middle stage
        ( E ) HAPLOTYPE: 2n
        ( F ) TISSUE TYPE:
        ( G ) CELL TYPE:
        ( H ) CELL LINE:
        ( I ) ORGANELLE: cotyledon ( v i i ) IMMEDIATE SOURCE:
        ( A ) LIBRARY: cDNA library
        ( B ) CLONE: A1B ( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY: Oat 12S globulin / 11- S protein family
        ( B ) LOCATION: protein bodies of cotyledonary tissue
        ( C ) IDENTIFICATION METHOD:
        ( D ) OTHER INFORMATION:

( x ) PUBLICATION INFORMATION:
        ( A ) AUTHORS:
        ( B ) TITLE:
        ( C ) JOURNAL:

( x i ) SEQUENCE DESCRIPTION: SEQ ID NO:2:

```
ACCATTCCAC CTTCTACAAT CTTTTCAAAC AATC ATG GCA ACT ACT AGT TTT CCA         55
                                     Met Ala Thr Thr Ser Phe Pro
                                                  -20

TCG GTA TTG TTT TAC TCT TGC ATT TTT CTC TTA TAC AAT GGA TCC ATG          103
Ser Val Leu Phe Tyr Ser Cys Ile Phe Leu Leu Tyr Asn Gly Ser Met
        -15                 -10                      -5

GCT CAA CTA TTC GGA CAG AGC TTT ACT CCA TGG CAA AGC TCT CGA CAA          151
Ala Gln Leu Phe Gly Gln Ser Phe Thr Pro Trp Gln Ser Ser Arg Gln
 1               5                    10                      15

GGA GGT TTA AAG GGG TGC AAA TTT GAT AGG CTG CAA GCA TTT GAA CCG          199
Gly Gly Leu Lys Gly Cys Lys Phe Asp Arg Leu Gln Ala Phe Glu Pro
                  20                  25                     30

CTT CGA CAA GTG AGG TCA CAA GCG GGT GTC ACT GAG TAC TTT GAT GAG          247
Leu Arg Gln Val Arg Ser Gln Ala Gly Val Thr Glu Tyr Phe Asp Glu
              35                  40                 45

CAG AAT GAG CAA TTA CGT TGT ACC GGG GTA TCT GTC ATT CGT CGT GTT          295
Gln Asn Glu Gln Leu Arg Cys Thr Gly Val Ser Val Ile Arg Arg Val
          50                  55                  60

ATT GAG CCC CAA GGC CTC TTG TTA CCT CAA TAC CAC AAC GCA CCC GGT          343
Ile Glu Pro Gln Gly Leu Leu Leu Pro Gln Tyr His Asn Ala Pro Gly
     65                   70                  75

CTG GTG TAC CTT CTT CAA GGT AGG GGT TTC ACG GGG TTG ACT TTA CCT          391
Leu Val Tyr Val Leu Gln Gly Arg Gly Phe Thr Gly Leu Thr Leu Pro
 80                   85                  90                      95

GGA TGT CCA GCG GCC TTC CAA CAA CAG TTC CAA CCA TTT GAT CGA GCC          439
Gly Cys Pro Ala Ala Phe Gln Gln Gln Phe Gln Pro Phe Asp Arg Ala
                 100                 105                 110

CAG GGT CAA AGC CAA AGC CAT CTC AAA GAT GAG CAC CAA AGA GTT CAC          487
Gln Gly Gln Ser Gln Ser His Leu Lys Asp Glu His Gln Arg Val His
             115                 120                 125

CGC TTT AAA CAA GGA GAT GTT ATT GCG CTG CCA GCT GGC ATT GTA CAC          535
Arg Phe Lys Gln Gly Asp Val Ile Ala Leu Pro Ala Gly Ile Val His
         130                 135                 140

TGG GGC TAC AAT GAT GGT GAT GCT CCA GTT GTA GCT ATC TAT GTC TTC          583
Trp Gly Tyr Asn Asp Gly Asp Ala Pro Val Val Ala Ile Tyr Val Phe
145                 150                 155

GAC GTA AAC AAC AAC GCT AAT CAA CTT GAA CCT AGA CAA AAG GAG TTC          631
Asp Val Asn Asn Asn Ala Asn Gln Leu Glu Pro Arg Gln Lys Glu Phe
160                 165                 170                 175

TTG TTG GCT GGT AAC AAT AAG GAT GAT CAA CAA TTT GGA CAA AAC ATA          679
Leu Leu Ala Gly Asn Asn Lys Asp Asp Gln Gln Phe Gly Gln Asn Ile
                 180                 185                 190

TTC AGC GGA TTC AAT ATC CAA CTT CTT AGT GAG GCT CTT GGT ATA AGT          727
Phe Ser Gly Phe Asn Ile Gln Leu Leu Ser Glu Ala Leu Gly Ile Ser
             195                 200                 205

CAA CAA GCA GCA CAG AGG ATC CAA AGT CAA AAG GAA CAA AGA GGT GAG          775
Gln Gln Ala Ala Gln Arg Ile Gln Ser Gln Lys Glu Gln Arg Gly Glu
         210                 215                 220

ATA ATT CGT GTG ACT CAA CGC CTT CAA TTC TTA AAG CCA ACA ATG TCC          823
Ile Ile Arg Val Thr Gln Arg Leu Gln Phe Leu Lys Pro Thr Met Ser
225                 230                 235

CAA CAA GAC AGA AGT TTC AAT GGT TTG GAG GAG AAC TTT TGT TCA TTG          871
Gln Gln Asp Arg Ser Phe Asn Gly Leu Glu Glu Asn Phe Cys Ser Leu
240                 245                 250                 255

GAG GCA AAG CAG AAC ATC GAA AAC CCC AAA CGT GCC GAC ACG TAC AAC          919
Glu Ala Lys Gln Asn Ile Glu Asn Pro Lys Arg Ala Asp Thr Tyr Asn
                 260                 265                 270

CCA CGT GCT GGT AGG ATA ACA CGT CTC CAT GGA CAG AAT TTC CCC ATC          967
```

|  |  |  |  |  |  |  |  |  |  |  |  |  |  |  |
|---|---|---|---|---|---|---|---|---|---|---|---|---|---|---|
| Pro | Arg | Ala | Gly<br>275 | Arg | Ile | Thr | Arg<br>280 | Leu | His | Gly | Gln | Asn<br>285 | Phe | Pro | Ile |

| CTT | AAC | CTC | GTG | CAA | ATG | AGC | GCC | ACA | AGA | GTA | AAT | CTA | TAC | CAG | AAT | 1015 |
|---|---|---|---|---|---|---|---|---|---|---|---|---|---|---|---|---|
| Leu | Asn<br>290 | Leu | Val | Gln | Met | Ser | Ala<br>295 | Thr | Arg | Val | Asn | Leu<br>300 | Tyr | Gln | Asn |  |

| GCT | ATT | CTT | TCA | CCA | TTC | TGG | AAC | ATC | AAT | GCA | CAT | AGT | GTG | GTC | TAC | 1063 |
|---|---|---|---|---|---|---|---|---|---|---|---|---|---|---|---|---|
| Ala | Ile<br>305 | Leu | Ser | Pro | Phe | Trp<br>310 | Asn | Ile | Asn | Ala | His<br>315 | Ser | Val | Val | Tyr |  |

| ATG | ATT | CAA | GGG | CAT | GCT | CGA | GTT | CAA | GTT | GTC | AAT | AAC | AAT | GGT | CAG | 1111 |
|---|---|---|---|---|---|---|---|---|---|---|---|---|---|---|---|---|
| Met<br>320 | Ile | Gln | Gly | His | Ala<br>325 | Arg | Val | Gln | Val | Val<br>330 | Asn | Asn | Asn | Gly | Gln<br>335 |  |

| ACT | GTA | TTC | AAT | GAC | CGT | CTT | CGC | CAA | GGT | CAG | TTG | CTA | ATC | TTA | CCA | 1159 |
|---|---|---|---|---|---|---|---|---|---|---|---|---|---|---|---|---|
| Thr | Val | Phe | Asn | Asp<br>340 | Arg | Leu | Arg | Gln | Gly<br>345 | Gln | Leu | Leu | Ile | Leu<br>350 | Pro |  |

| CAA | CAC | TAC | GTT | GTT | CTC | AAG | AAG | ACG | GAG | CGT | GAA | GGA | TGC | CAG | TAT | 1207 |
|---|---|---|---|---|---|---|---|---|---|---|---|---|---|---|---|---|
| Gln | His | Tyr | Val | Val<br>355 | Leu | Lys | Lys | Thr | Glu<br>360 | Arg | Glu | Gly | Cys | Gln<br>365 | Tyr |  |

| ATC | TCA | TTC | AAG | ACC | AAC | CCA | AAC | TCC | ATG | GTT | AGC | CAC | ATT | GCT | GGA | 1255 |
|---|---|---|---|---|---|---|---|---|---|---|---|---|---|---|---|---|
| Ile | Ser | Phe<br>370 | Lys | Thr | Asn | Pro | Asn<br>375 | Ser | Met | Val | Ser | His<br>380 | Ile | Ala | Gly |  |

| AAG | AGC | TCC | ATT | CTT | CGT | GCC | TTG | CCC | GTG | AAT | GTC | CTC | GCC | AAT | GCA | 1303 |
|---|---|---|---|---|---|---|---|---|---|---|---|---|---|---|---|---|
| Lys | Ser<br>385 | Ser | Ile | Leu | Arg | Ala<br>390 | Leu | Pro | Val | Asn | Val<br>395 | Leu | Ala | Asn | Ala |  |

| TAC | CGC | ATT | TCC | AGG | CAA | GAA | GTC | CGA | AAC | CTC | AAA | AAC | AAC | AGG | GGA | 1351 |
|---|---|---|---|---|---|---|---|---|---|---|---|---|---|---|---|---|
| Tyr<br>400 | Arg | Ile | Ser | Arg | Gln<br>405 | Glu | Val | Arg | Asn | Leu<br>410 | Lys | Asn | Asn | Arg | Gly<br>415 |  |

| CAA | GAG | TCT | GGT | GTA | TTC | ACT | CCA | AAA | TTT | ACC | CAA | ACG | AGC | TTC | CAA | 1399 |
|---|---|---|---|---|---|---|---|---|---|---|---|---|---|---|---|---|
| Gln | Glu | Ser | Gly | Val<br>420 | Phe | Thr | Pro | Lys | Phe<br>425 | Thr | Gln | Thr | Ser | Phe<br>430 | Gln |  |

| CCT | TAT | CCA | GAG | GGC | GAG | GAT | GAG | TCA | TCT | TTG | ATT | AAT | AAG | GCA | TCA | 1447 |
|---|---|---|---|---|---|---|---|---|---|---|---|---|---|---|---|---|
| Pro | Tyr | Pro | Glu<br>435 | Gly | Glu | Asp | Glu | Ser<br>440 | Ser | Leu | Ile | Asn | Lys<br>445 | Ala | Ser |  |

| GAG | TAAATTAGTG | AGTGTGATGA | GGACCAATAT | AGTGAAATAA | AAGCATCGCA | 1500 |
|---|---|---|---|---|---|---|
| Glu |  |  |  |  |  |  |

| AGTGTGGAAG | TGGGTGGTAT | ATAACCGCTT | ATCTTAATAA | ATAACTTCAT | CATGTT | 1556 |
|---|---|---|---|---|---|---|

( 2 ) INFORMATION FOR SEQ ID NO:3:

( i ) SEQUENCE CHARACTERISTICS:
        ( A ) LENGTH: 4 amino acids
        ( B ) TYPE: amino acid
        ( C ) STRANDEDNESS:
        ( D ) TOPOLOGY: linear ( i i ) MOLECULE TYPE:

( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

(viii) POSITION IN GENOME:
    (A) CHROMOSOME/SEGMENT:
    (B) MAP POSITION:
    (C) UNITS:

(ix) FEATURE:
    (A) NAME/KEY:
    (B) LOCATION:
    (C) IDENTIFICATION METHOD:
    (D) OTHER INFORMATION:

(x) PUBLICATION INFORMATION:
    (A) AUTHORS:
    (B) TITLE:
    (C) JOURNAL:

(xi) SEQUENCE DESCRIPTION: SEQ ID NO:3:

Pro Glu Ala Asn
    1

(2) INFORMATION FOR SEQ ID NO:4:

(i) SEQUENCE CHARACTERISTICS:
    (A) LENGTH: 6 amino acids
    (B) TYPE: amino acid
    (C) STRANDEDNESS:
    (D) TOPOLOGY: linear (ii) MOLECULE TYPE:

(iii) HYPOTHETICAL:

(iv) ANTI-SENSE:

(v) FRAGMENT TYPE:

(vi) ORIGINAL SOURCE:
    (A) ORGANISM:
    (B) STRAIN:
    (C) INDIVIDUAL ISOLATE:
    (D) DEVELOPMENTAL STAGE:
    (E) HAPLOTYPE:
    (F) TISSUE TYPE:
    (G) CELL TYPE:
    (H) CELL LINE:
    (I) ORGANELLE:;

(vii) IMMEDIATE SOURCE:
    (A) LIBRARY:
    (B) CLONE:

(viii) POSITION IN GENOME:
    (A) CHROMOSOME/SEGMENT:
    (B) MAP POSITION:
    (C) UNITS:

(ix) FEATURE:
    (A) NAME/KEY:
    (B) LOCATION:
    (C) IDENTIFICATION METHOD:
    (D) OTHER INFORMATION:

(x) PUBLICATION INFORMATION:
    (A) AUTHORS:
    (B) TITLE:
    (C) JOURNAL:

(xi) SEQUENCE DESCRIPTION: SEQ ID NO:4:

Gly Leu Glu Glu Asn Phe
    1                5

(2) INFORMATION FOR SEQ ID NO:5:

(i) SEQUENCE CHARACTERISTICS:
    (A) LENGTH: 7 amino acids
    (B) TYPE: amino acid ( C ) STRANDEDNESS:
            ( D ) TOPOLOGY: linear ( i i ) MOLECULE TYPE:

( i i i ) HYPOTHETICAL:

( i v ) ANTI-SENSE:

( v ) FRAGMENT TYPE:

( v i ) ORIGINAL SOURCE:
            ( A ) ORGANISM:
            ( B ) STRAIN:
            ( C ) INDIVIDUAL ISOLATE:
            ( D ) DEVELOPMENTAL STAGE:
            ( E ) HAPLOTYPE:
            ( F ) TISSUE TYPE:
            ( G ) CELL TYPE:
            ( H ) CELL LINE:
            ( I ) ORGANELLE:;

( v i i ) IMMEDIATE SOURCE:
            ( A ) LIBRARY:
            ( B ) CLONE:

( v i i i ) POSITION IN GENOME:
            ( A ) CHROMOSOME/SEGMENT:
            ( B ) MAP POSITION:
            ( C ) UNITS:

( i x ) FEATURE:
            ( A ) NAME/KEY:
            ( B ) LOCATION:
            ( C ) IDENTIFICATION METHOD:
            ( D ) OTHER INFORMATION:

( x ) PUBLICATION INFORMATION:
            ( A ) AUTHORS:
            ( B ) TITLE:
            ( C ) JOURNAL:

( x i ) SEQUENCE DESCRIPTION: SEQ ID NO:5:

Asn  Asn  Asn  Val  Glu  Glu  Leu
             1                    5

( 2 ) INFORMATION FOR SEQ ID NO:6:

( i ) SEQUENCE CHARACTERISTICS:
            ( A ) LENGTH: 8 amino acids
            ( B ) TYPE: amino acid
            ( C ) STRANDEDNESS:
            ( D ) TOPOLOGY: linear ( i i ) MOLECULE TYPE:

( i i i ) HYPOTHETICAL:

( i v ) ANTI-SENSE:

( v ) FRAGMENT TYPE:

( v i ) ORIGINAL SOURCE:
            ( A ) ORGANISM:
            ( B ) STRAIN:
            ( C ) INDIVIDUAL ISOLATE:
            ( D ) DEVELOPMENTAL STAGE:
            ( E ) HAPLOTYPE:
            ( F ) TISSUE TYPE:
            ( G ) CELL TYPE:
            ( H ) CELL LINE:
            ( I ) ORGANELLE:;

( v i i ) IMMEDIATE SOURCE:
            ( A ) LIBRARY:
            ( B ) CLONE:

( v i i i ) POSITION IN GENOME:

(A) CHROMOSOME/SEGMENT:
                (B) MAP POSITION:
                (C) UNITS:

(ix) FEATURE:
                (A) NAME/KEY:
                (B) LOCATION:
                (C) IDENTIFICATION METHOD:
                (D) OTHER INFORMATION:

(x) PUBLICATION INFORMATION:
                (A) AUTHORS:
                (B) TITLE:
                (C) JOURNAL:

(xi) SEQUENCE DESCRIPTION: SEQ ID NO:6:

Asn  Asn  Asn  Asn  Val  Glu  Glu  Leu
                 1                    5

(2) INFORMATION FOR SEQ ID NO:7:

(i) SEQUENCE CHARACTERISTICS:
                (A) LENGTH: 7 amino acids
                (B) TYPE: amino acid
                (C) STRANDEDNESS:
                (D) TOPOLOGY: linear (ii) MOLECULE TYPE:

(iii) HYPOTHETICAL:

(iv) ANTI-SENSE:

(v) FRAGMENT TYPE:

(vi) ORIGINAL SOURCE:
                (A) ORGANISM:
                (B) STRAIN:
                (C) INDIVIDUAL ISOLATE:
                (D) DEVELOPMENTAL STAGE:
                (E) HAPLOTYPE:
                (F) TISSUE TYPE:
                (G) CELL TYPE:
                (H) CELL LINE:
                (I) ORGANELLE:;

(vii) IMMEDIATE SOURCE:
                (A) LIBRARY:
                (B) CLONE:

(viii) POSITION IN GENOME:
                (A) CHROMOSOME/SEGMENT:
                (B) MAP POSITION:
                (C) UNITS:

(ix) FEATURE:
                (A) NAME/KEY:
                (B) LOCATION:
                (C) IDENTIFICATION METHOD:
                (D) OTHER INFORMATION:

(x) PUBLICATION INFORMATION:
                (A) AUTHORS:
                (B) TITLE:
                (C) JOURNAL:

(xi) SEQUENCE DESCRIPTION: SEQ ID NO:7:

Asn  Asn  Asn  Ser  Glu  Glu  Leu
                 1                    5

(2) INFORMATION FOR SEQ ID NO:8:

(i) SEQUENCE CHARACTERISTICS:
                (A) LENGTH: 7 amino acids
                (B) TYPE: amino acid
                (C) STRANDEDNESS:

(D) TOPOLOGY: linear (ii) MOLECULE TYPE:

(iii) HYPOTHETICAL:

(iv) ANTI-SENSE:

(v) FRAGMENT TYPE:

(vi) ORIGINAL SOURCE:
    (A) ORGANISM:
    (B) STRAIN:
    (C) INDIVIDUAL ISOLATE:
    (D) DEVELOPMENTAL STAGE:
    (E) HAPLOTYPE:
    (F) TISSUE TYPE:
    (G) CELL TYPE:
    (H) CELL LINE:
    (I) ORGANELLE:;

(vii) IMMEDIATE SOURCE:
    (A) LIBRARY:
    (B) CLONE:

(viii) POSITION IN GENOME:
    (A) CHROMOSOME/SEGMENT:
    (B) MAP POSITION:
    (C) UNITS:

(ix) FEATURE:
    (A) NAME/KEY:
    (B) LOCATION:
    (C) IDENTIFICATION METHOD:
    (D) OTHER INFORMATION:

(x) PUBLICATION INFORMATION:
    (A) AUTHORS:
    (B) TITLE:
    (C) JOURNAL:

(xi) SEQUENCE DESCRIPTION: SEQ ID NO:8:

Asn  Asn  Asn  Glu  Val  Glu  Leu
    1                        5

(2) INFORMATION FOR SEQ ID NO:9:

(i) SEQUENCE CHARACTERISTICS:
    (A) LENGTH: 10 amino acids
    (B) TYPE: amino acid
    (C) STRANDEDNESS:
    (D) TOPOLOGY: linear (ii) MOLECULE TYPE:

(iii) HYPOTHETICAL:

(iv) ANTI-SENSE:

(v) FRAGMENT TYPE:

(vi) ORIGINAL SOURCE:
    (A) ORGANISM:
    (B) STRAIN:
    (C) INDIVIDUAL ISOLATE:
    (D) DEVELOPMENTAL STAGE:
    (E) HAPLOTYPE:
    (F) TISSUE TYPE:
    (G) CELL TYPE:
    (H) CELL LINE:
    (I) ORGANELLE:;

(vii) IMMEDIATE SOURCE:
    (A) LIBRARY:
    (B) CLONE:

(viii) POSITION IN GENOME:
    (A) CHROMOSOME/SEGMENT:

(B) MAP POSITION:
            (C) UNITS:

(ix) FEATURE:
            (A) NAME/KEY:
            (B) LOCATION:
            (C) IDENTIFICATION METHOD:
            (D) OTHER INFORMATION:

(x) PUBLICATION INFORMATION:
            (A) AUTHORS:
            (B) TITLE:
            (C) JOURNAL:

(xi) SEQUENCE DESCRIPTION: SEQ ID NO:9:

Ser  Glu  Ser  Glu  Asn  Gly  Leu  Glu  Glu  Thr
        1                   5                        10

(2) INFORMATION FOR SEQ ID NO:10:

(i) SEQUENCE CHARACTERISTICS:
            (A) LENGTH: 7 amino acids
            (B) TYPE: amino acid
            (C) STRANDEDNESS:
            (D) TOPOLOGY: linear (ii) MOLECULE TYPE:

(iii) HYPOTHETICAL:

(iv) ANTI-SENSE:

(v) FRAGMENT TYPE:

(vi) ORIGINAL SOURCE:
            (A) ORGANISM:
            (B) STRAIN:
            (C) INDIVIDUAL ISOLATE:
            (D) DEVELOPMENTAL STAGE:
            (E) HAPLOTYPE:
            (F) TISSUE TYPE:
            (G) CELL TYPE:
            (H) CELL LINE:
            (I) ORGANELLE:;

(vii) IMMEDIATE SOURCE:
            (A) LIBRARY:
            (B) CLONE:

(viii) POSITION IN GENOME:
            (A) CHROMOSOME/SEGMENT:
            (B) MAP POSITION:
            (C) UNITS:

(ix) FEATURE:
            (A) NAME/KEY:
            (B) LOCATION:
            (C) IDENTIFICATION METHOD:
            (D) OTHER INFORMATION:

(x) PUBLICATION INFORMATION:
            (A) AUTHORS:
            (B) TITLE:
            (C) JOURNAL:

(xi) SEQUENCE DESCRIPTION: SEQ ID NO:10:

Phe  Asn  Asn  Val  Glu  Glu  Leu
        1                   5

(2) INFORMATION FOR SEQ ID NO:11:

(i) SEQUENCE CHARACTERISTICS:
            (A) LENGTH: 7 amino acids
            (B) TYPE: amino acid
            (C) STRANDEDNESS:
            (D) TOPOLOGY: linear ( i i ) MOLECULE TYPE:

( i i i ) HYPOTHETICAL:

( i v ) ANTI-SENSE:

( v ) FRAGMENT TYPE:

( v i ) ORIGINAL SOURCE:
               ( A ) ORGANISM:
               ( B ) STRAIN:
               ( C ) INDIVIDUAL ISOLATE:
               ( D ) DEVELOPMENTAL STAGE:
               ( E ) HAPLOTYPE:
               ( F ) TISSUE TYPE:
               ( G ) CELL TYPE:
               ( H ) CELL LINE:
               ( I ) ORGANELLE:;

( v i i ) IMMEDIATE SOURCE:
               ( A ) LIBRARY:
               ( B ) CLONE:

( v i i i ) POSITION IN GENOME:
               ( A ) CHROMOSOME/SEGMENT:
               ( B ) MAP POSITION:
               ( C ) UNITS:

( i x ) FEATURE:
               ( A ) NAME/KEY:
               ( B ) LOCATION:
               ( C ) IDENTIFICATION METHOD:
               ( D ) OTHER INFORMATION:

( x ) PUBLICATION INFORMATION:
               ( A ) AUTHORS:
               ( B ) TITLE:
               ( C ) JOURNAL:

( x i ) SEQUENCE DESCRIPTION: SEQ ID NO:11:

Asn  Asn  Asn  Leu  Glu  Glu  Leu
            1                 5

( 2 ) INFORMATION FOR SEQ ID NO:12:

( i ) SEQUENCE CHARACTERISTICS:
               ( A ) LENGTH: 7 amino acids
               ( B ) TYPE: amino acid
               ( C ) STRANDEDNESS:
               ( D ) TOPOLOGY: linear ( i i ) MOLECULE TYPE:

( i i i ) HYPOTHETICAL:

( i v ) ANTI-SENSE:

( v ) FRAGMENT TYPE:

( v i ) ORIGINAL SOURCE:
               ( A ) ORGANISM:
               ( B ) STRAIN:
               ( C ) INDIVIDUAL ISOLATE:
               ( D ) DEVELOPMENTAL STAGE:
               ( E ) HAPLOTYPE:
               ( F ) TISSUE TYPE:
               ( G ) CELL TYPE:
               ( H ) CELL LINE:
               ( I ) ORGANELLE:;

( v i i ) IMMEDIATE SOURCE:
               ( A ) LIBRARY:
               ( B ) CLONE:

( v i i i ) POSITION IN GENOME:
               ( A ) CHROMOSOME/SEGMENT:
               ( B ) MAP POSITION:

(C) UNITS:

(ix) FEATURE:
    (A) NAME/KEY:
    (B) LOCATION:
    (C) IDENTIFICATION METHOD:
    (D) OTHER INFORMATION:

(x) PUBLICATION INFORMATION:
    (A) AUTHORS:
    (B) TITLE:
    (C) JOURNAL:

(xi) SEQUENCE DESCRIPTION: SEQ ID NO:12:

```
Asn  Asn  Asn  Glu  Leu  Glu  Leu
 1                  5
```

(2) INFORMATION FOR SEQ ID NO:13:

(i) SEQUENCE CHARACTERISTICS:
    (A) LENGTH: 7 amino acid
    (B) TYPE: amino acid
    (C) STRANDEDNESS:
    (D) TOPOLOGY: linear (ii) MOLECULE TYPE:

(iii) HYPOTHETICAL:

(iv) ANTI-SENSE:

(v) FRAGMENT TYPE:

(vi) ORIGINAL SOURCE:
    (A) ORGANISM:
    (B) STRAIN:
    (C) INDIVIDUAL ISOLATE:
    (D) DEVELOPMENTAL STAGE:
    (E) HAPLOTYPE:
    (F) TISSUE TYPE:
    (G) CELL TYPE:
    (H) CELL LINE:
    (I) ORGANELLE:;

(vii) IMMEDIATE SOURCE:
    (A) LIBRARY:
    (B) CLONE:

(viii) POSITION IN GENOME:
    (A) CHROMOSOME/SEGMENT:
    (B) MAP POSITION:
    (C) UNITS:

(ix) FEATURE:
    (A) NAME/KEY:
    (B) LOCATION:
    (C) IDENTIFICATION METHOD:
    (D) OTHER INFORMATION:

(x) PUBLICATION INFORMATION:
    (A) AUTHORS:
    (B) TITLE:
    (C) JOURNAL:

(xi) SEQUENCE DESCRIPTION: SEQ ID NO:13:

```
Asn  Asn  Asn  Ile  Glu  Glu  Leu
 1                  5
```

(2) INFORMATION FOR SEQ ID NO:14:

(i) SEQUENCE CHARACTERISTICS:
    (A) LENGTH: 7 amino acids
    (B) TYPE: amino acid
    (C) STRANDEDNESS:
    (D) TOPOLOGY: linear ( i i ) MOLECULE TYPE:

( i i i ) HYPOTHETICAL:

( i v ) ANTI-SENSE:

( v ) FRAGMENT TYPE:

( v i ) ORIGINAL SOURCE:
    ( A ) ORGANISM:
    ( B ) STRAIN:
    ( C ) INDIVIDUAL ISOLATE:
    ( D ) DEVELOPMENTAL STAGE:
    ( E ) HAPLOTYPE:
    ( F ) TISSUE TYPE:
    ( G ) CELL TYPE:
    ( H ) CELL LINE:
    ( I ) ORGANELLE:;

( v i i ) IMMEDIATE SOURCE:
    ( A ) LIBRARY:
    ( B ) CLONE:

( v i i i ) POSITION IN GENOME:
    ( A ) CHROMOSOME/SEGMENT:
    ( B ) MAP POSITION:
    ( C ) UNITS:

( i x ) FEATURE:
    ( A ) NAME/KEY:
    ( B ) LOCATION:
    ( C ) IDENTIFICATION METHOD:
    ( D ) OTHER INFORMATION:

( x ) PUBLICATION INFORMATION:
    ( A ) AUTHORS:
    ( B ) TITLE:
    ( C ) JOURNAL:

( x i ) SEQUENCE DESCRIPTION: SEQ ID NO:14:

```
Asn  Asn  Asn  Glu  Ile  Glu  Leu
 1                    5
```

( 2 ) INFORMATION FOR SEQ ID NO:15:

( i ) SEQUENCE CHARACTERISTICS:
        ( A ) LENGTH: 24 amino acid
        ( B ) TYPE: amino acids
        ( C ) STRANDEDNESS:
        ( D ) TOPOLOGY: linear ( i i ) MOLECULE TYPE:

( i i i ) HYPOTHETICAL:

( i v ) ANTI-SENSE:

( v ) FRAGMENT TYPE:

( v i ) ORIGINAL SOURCE:
    ( A ) ORGANISM:
    ( B ) STRAIN:
    ( C ) INDIVIDUAL ISOLATE:
    ( D ) DEVELOPMENTAL STAGE:
    ( E ) HAPLOTYPE:
    ( F ) TISSUE TYPE:
    ( G ) CELL TYPE:
    ( H ) CELL LINE:
    ( I ) ORGANELLE:;

( v i i ) IMMEDIATE SOURCE:
    ( A ) LIBRARY:
    ( B ) CLONE:

( v i i i ) POSITION IN GENOME:
    ( A ) CHROMOSOME/SEGMENT:
    ( B ) MAP POSITION:
    ( C ) UNITS:

( i x ) FEATURE:
    ( A ) NAME/KEY:
    ( B ) LOCATION:
    ( C ) IDENTIFICATION METHOD:
    ( D ) OTHER INFORMATION:

( x ) PUBLICATION INFORMATION:
    ( A ) AUTHORS:
    ( B ) TITLE:
    ( C ) JOURNAL:

( x i ) SEQUENCE DESCRIPTION: SEQ ID NO:15:

His Ser Asp Ala Val Phe Thr Asp Asn Tyr Thr Arg Leu Arg Lys Gln
 1               5                  10                  15

Met Ala Val Lys Lys Tyr Leu Asn
             20

( 2 ) INFORMATION FOR SEQ ID NO:16:

( i ) SEQUENCE CHARACTERISTICS:
        ( A ) LENGTH: 15 amino acids
        ( B ) TYPE: amino acid
        ( C ) STRANDEDNESS:
        ( D ) TOPOLOGY: linear ( i i ) MOLECULE TYPE:

( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:;

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION:
        ( C ) IDENTIFICATION METHOD:
        ( D ) OTHER INFORMATION:

( x ) PUBLICATION INFORMATION:
        ( A ) AUTHORS:
        ( B ) TITLE:
        ( C ) JOURNAL:

( x i ) SEQUENCE DESCRIPTION: SEQ ID NO:16:

Tyr Thr Arg Leu Arg Lys Gln Met Ala Val Lys Lys Tyr Leu Asn
 1               5                  10                  15

( 2 ) INFORMATION FOR SEQ ID NO:17:

( i ) SEQUENCE CHARACTERISTICS:
        ( A ) LENGTH: 9 amino acids
        ( B ) TYPE: amino acid
        ( C ) STRANDEDNESS:

(D) TOPOLOGY: linear (ii) MOLECULE TYPE:

(iii) HYPOTHETICAL:

(iv) ANTI-SENSE:

(v) FRAGMENT TYPE:

(vi) ORIGINAL SOURCE:
    (A) ORGANISM:
    (B) STRAIN:
    (C) INDIVIDUAL ISOLATE:
    (D) DEVELOPMENTAL STAGE:
    (E) HAPLOTYPE:
    (F) TISSUE TYPE:
    (G) CELL TYPE:
    (H) CELL LINE:
    (I) ORGANELLE:;

(vii) IMMEDIATE SOURCE:
    (A) LIBRARY:
    (B) CLONE:

(viii) POSITION IN GENOME:
    (A) CHROMOSOME/SEGMENT:
    (B) MAP POSITION:
    (C) UNITS:

(ix) FEATURE:
    (A) NAME/KEY:
    (B) LOCATION:
    (C) IDENTIFICATION METHOD:
    (D) OTHER INFORMATION:

(x) PUBLICATION INFORMATION:
    (A) AUTHORS:
    (B) TITLE:
    (C) JOURNAL:

(xi) SEQUENCE DESCRIPTION: SEQ ID NO:17:

His  Ser  Asp  Ala  Val  Phe  Thr  Asp  Asn
    1                        5

(2) INFORMATION FOR SEQ ID NO:18:

(i) SEQUENCE CHARACTERISTICS:
    (A) LENGTH: 4 amino acids
    (B) TYPE: amino acid
    (C) STRANDEDNESS: single
    (D) TOPOLOGY: linear (xi) SEQUENCE DESCRIPTION: SEQ ID NO:18:

Glu  Val  Glu  Leu
    1

(2) INFORMATION FOR SEQ ID NO:19:

(i) SEQUENCE CHARACTERISTICS:
    (A) LENGTH: 6 amino acids
    (B) TYPE: amino acid
    (C) STRANDEDNESS: single
    (D) TOPOLOGY: linear (xi) SEQUENCE DESCRIPTION: SEQ ID NO:19:

Asn  Asn  Val  Glu  Glu  Leu
    1                    5

(2) INFORMATION FOR SEQ ID NO:20:

(i) SEQUENCE CHARACTERISTICS:
    (A) LENGTH: 5 amino acids
    (B) TYPE: amino acid

```
        ( C ) STRANDEDNESS: single
        ( D ) TOPOLOGY: linear ( x i ) SEQUENCE DESCRIPTION: SEQ ID NO:20:

Asn Val Glu Glu Leu
        1               5

( 2 ) INFORMATION FOR SEQ ID NO:21:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:21:

GCTTAATTAA TTAAGC                                                16

( 2 ) INFORMATION FOR SEQ ID NO:22:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:22:

CGAATTAATT AATTCG                                                16
```

METHOD FOR PRODUCING AN ASPARAGINYL ENDOPROTEASE

This is a division of application Ser. No. 08/091,991 filed Jul. 12, 1993 (abandoned).

FIELD OF THE INVENTION

The present invention relates to a novel asparaginyl endoprotease, a method for its production and a method for its use.

DESCRIPTION OF THE PRIOR ART

Plant seeds, including soybean seeds, contain storage proteins and thus have been used for years as protein sources. Of storage proteins, particularly glycinin storage proteins are the major proteins, and they have an important influence on the physical properties and texture of said protein sources.

These glycinin storage proteins, as shown in FIG. 1, comprise an acidic and basic subunit pair, and are synthesized as prepro-proteins after their expression, by specific cleavage between the two subunits by a protease, i.e., asparaginyl endoprotease according to the present invention. For the practical use of these important protein sources, conventionally their genes have been expressed in microorganisms in an attempt at mass production of said proteins. However, the proteins produced by microorganisms are precursors, and no method has been developed for their maturation.

SUBJECT MATTER OF THE INVENTION

We the present inventors, as a result of diligent research aimed at establishing a method for the maturation of a glycinin storage protein precursor produced by a microorganism, have discovered a novel asparaginyl endoprotease which is capable of maturing the precursor, and upon confirmation of the properties thereof, the present invention has been completed.

BRIEF DESCRIPTION OF THE DRAWINGS

FIGS. 6A to 6G (SEQ ID NOS. 1 and 2) show the base sequence of cDNA of the oat 12S globulin $A_2B$ used in Reference 2. The clone named pOTG664 is the cDNA which codes for $A_2B$. The section downstream from the * was introduced into an expression vector according to the method illustrated in FIG. 7, and $E.\ coli$ was used for the production.

In FIG. 8A is an analysis diagram from Western blotting performed after allowing an enzyme to act on the oat 12S globulin precursor in Example 5. 58 K indicates the oat 12S globulin precursor pro-$A_2B$, and 33 K indicates the $A_2$ acidic subunit of oat 12S globulin. In the diagram, "a" indicates the oat 12S globulin fraction (the protein extracted from oat seeds. As is clear from the cDNA base sequence in FIG. 6, oat 12S proteins of varying sizes are synthesized by groups of mRNA which lack the C-terminus of the acidic subunit to varying degrees. The $A_2$ acidic subunit is the protein thereof with the greatest molecular size;

Figure 1:
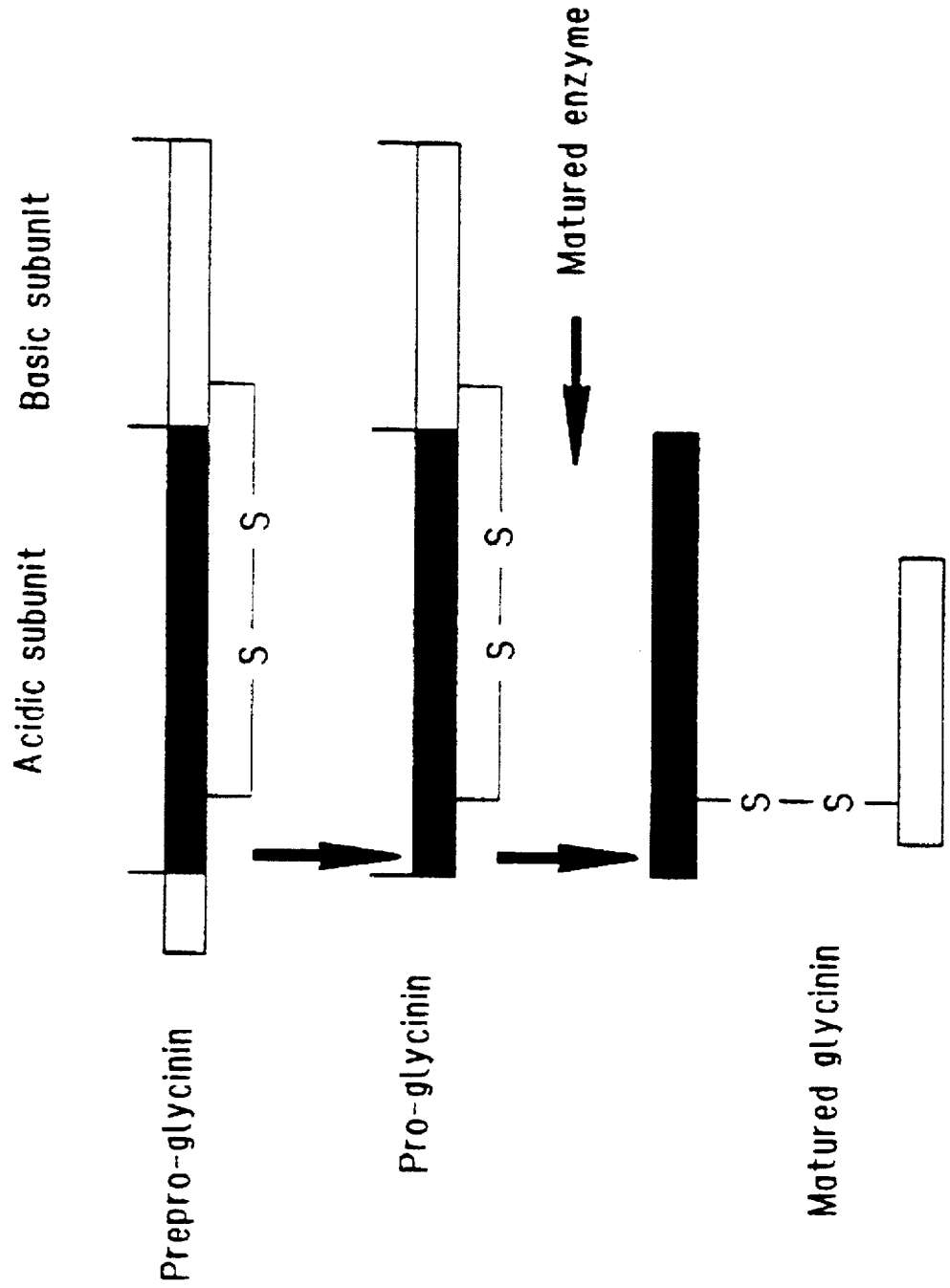
FIG. 1 is a schematic diagram of the processing of a glycinin storage protein by a protease.

"b" indicates pro-$A_2B$;

"c" indicates the fraction which was not reacted by addition of the crude enzyme solution of asparaginyl endoprotease taken from oats to pro-$A_2B$ (control experiment).

"d" indicates the fraction which was reacted by addition of the same enzyme solution as for "c" above to pro-$A_2B$;

"e" indicates the fraction resulting from the reaction of purified soybean enzyme with pro-$A_2B$;

"f" indicates the fraction resulting from the reaction of crude wisteria enzyme with pro-$A_2B$;

"g" indicates the fraction resulting from the reaction of crude genista enzyme with pro-$A_2B$;

"h" indicates the fraction resulting from the reaction of crude pagoda enzyme with pro-$A_2B$;

"i" indicates the fraction resulting from the reaction of crude sasanqua enzyme with pro-$A_2B$;

"j" indicates the fraction resulting from the reaction of crude phoenix enzyme with pro-$A_2B$;

"k" indicates the fraction resulting from the reaction of crude camellia enzyme with pro-$A_2B$;

"l" indicates the fraction resulting from the reaction of crude tobacco enzyme with pro-$A_2B$;

"m" indicates the fraction resulting from the reaction of purified rice enzyme with pro-$A_2B$;

"n" indicates the fraction resulting from the reaction of crude wheat enzyme with pro-$A_2B$;

"o" indicates the fraction resulting from the reaction of crude corn enzyme with pro-$A_2B$;

"p" indicates the fraction resulting from the reaction of crude barley enzyme with pro-$A_2B$;

"q" indicates the fraction resulting from the reaction of purified ginkgo nut enzyme with pro-$A_2B$;

"r" indicates the fraction resulting from the reaction of crude glycine soja with pro-$A_2B$; and "s" indicates the fraction resulting from the reaction with $A_2B$ alone, with no addition of enzyme (comparison).

FIG. 8B is a typical cleavage pattern of purified oat 12S globulin after treatment with purified soybean enzyme, revealed by a CBB staining. In FIG. 8A, the immunoblot method was used to show that enzymes from different sources had a high possibility of cleaving the same site of the same substrate. The antibodies used were those produced against oat 12S globulin, but they reacted only with the acidic subunit of oat 12S globulin, and not with the basic subunit thereof. In diagram B, the results are shown of an experiment which was conducted in order to reveal whether the enzyme prepared from the seeds of plants other than oats would cleave the oat precursor precisely after the asparagine residue assumed to be present at the site of bonding of the acidic subunit and the basic subunit. The purified oat 12S globulin pro-$A_2B$ protein (60 µg) was cleaved by the asparaginyl endoprotease (2 µg) purified from soybeans. Thereafter, the N-terminus of the amino acid sequence of the fragment which was thought to correspond to the basic subunit separated by SDS-PAGE, was analyzed using a gas-phase amino acid sequencer (ABI Co., U.S.A.), according to the method in Example 4. The "*" indicates pro-$A_2B$, and the "**" indicates the acidic subunit $A_2$ which was cleaved by the enzyme.

Figure 9:
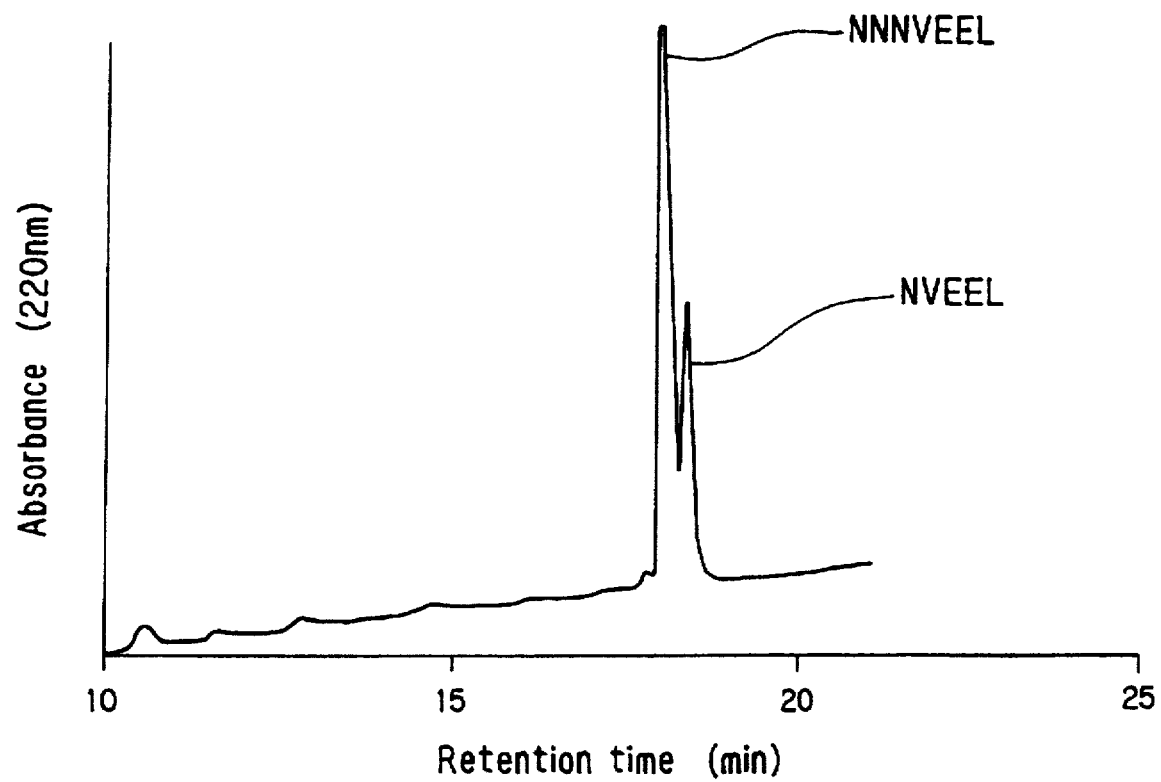
Figure 9:
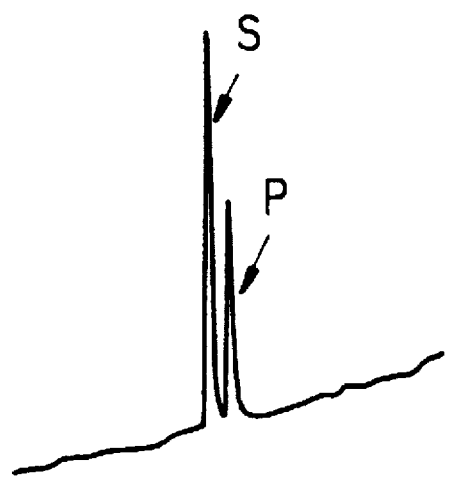

FIGS. 9A and 9B show an HPLC pattern showing the rules of decomposition of a synthetic peptide by the enzyme in Example 6. The FIG. 9A shows the decomposition pattern for the peptide NNNVEEL (SEQ ID NO:5), and the FIG. 9B shows the decomposition pattern for the peptide NNNEVEL (SEQ ID NO:8). In FIG. 9A NVEEL is SEQ ID NO: 20. S indicates NNNEVEL (SEQ ID NO:8), and P indicates EVEL (SEQ ID NO:18).

Figure 10:
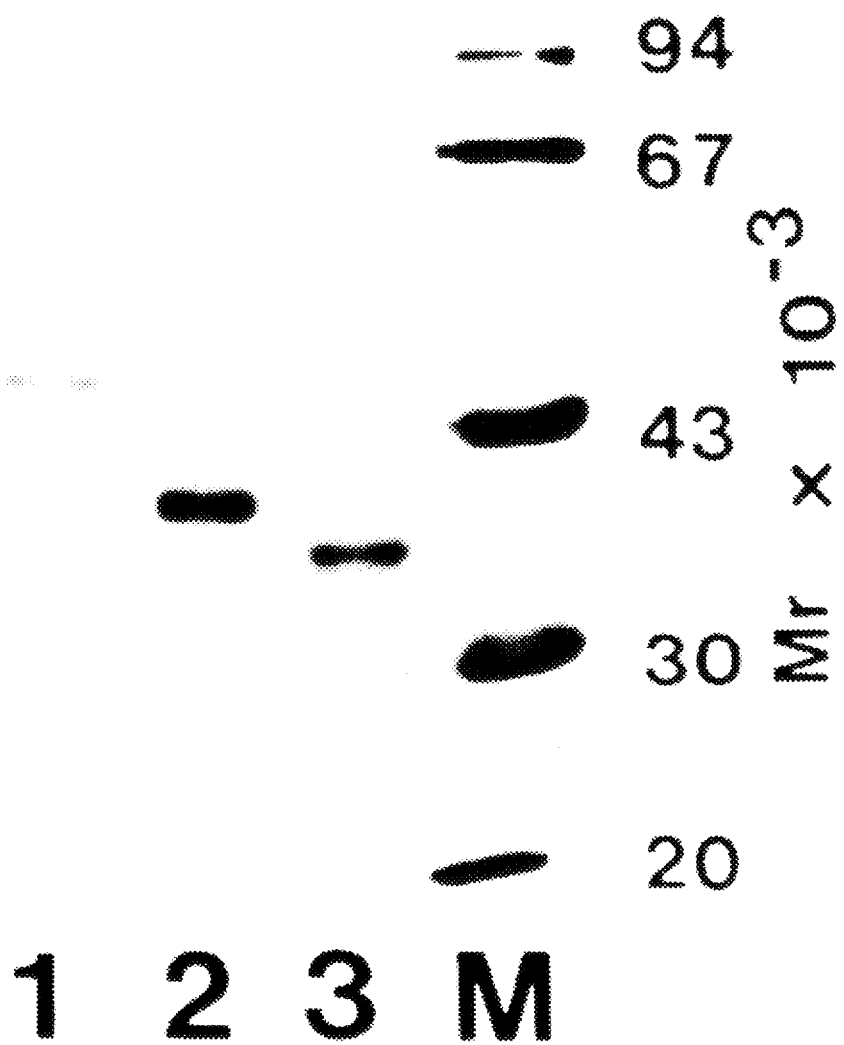

FIG. 10 is an SDS-gel electrophoresis image of the enzyme in Example 6, wherein M indicates a molecular weight marker, lane 1 indicates purified enzyme from rice (molecular weight approximately 45K daltons), lane 2 indicates purified enzyme from ginkgo (molecular weight approximately 37K daltons), and lane 3 indicates purified enzyme from soybean (molecular weight approximately 33–34K daltons).

SUMMARY OF THE INVENTION

First, the present invention relates to a novel asparaginyl endoprotease which is obtained from the seeds of angiosperms or gymnosperms, and which possesses the physicochemical properties described below.

(1) It acts on glycinin storage proteins or related protein precursors, causing hydrolysis exactly between the C-terminal amino acid residue of the acidic subunit region, Asn, and the N-terminal amino acid residue of the basic subunit region, Gly or Asn.

(2) Its operative pH is 4.0 to 7.0.

(3) It is thiolytic (4) It is a simple protein of molecular weight 33 KDa to 46 KDa, with no sugar chains which imply that the enzyme is not adsorbed onto concanavalin A-Sepharose column.

(5) It acts on peptides or denatured proteins, and hydrolyses the peptide bond on the carboxyl end of the asparagine residue, while the enzyme does not cleave the following synthetic substrates containing asparaginyl residue; Boc-Asn-4-nitrophenyl ester, DNP-Pro-Glu-Ala-Asn-$NH_2$ (SEQ ID NO:3) and Z-Ala-Ala-Asn-$NH_2$.

(6) It is synthesized mainly at the early stage of seed embryogenesis and is degraded in early imbibition; for example, both the enzyme and the activity employing proglycinin disappear completely after 12h-imbibition (demonstrated in an immunological sense and an immunoblotting).

Furthermore, the present invention relates to a method for the production of a novel asparaginyl endoprotease, characterized by extracting ground seeds of an angiosperm or gymnosperm taken between the early growing stage and the ripe stage, using a buffer solution at pH 4.0–6.0, dialyzing the soluble fraction, and then separating the solid and liquid, as well as to a method for the production of a glycinin storage protein, characterized by allowing the above mentioned enzyme to act on the glycinin storage protein precursor.

As mentioned above, the novel asparaginyl endoprotease according to the present invention may be obtained from the seeds of angiosperms or gymnosperms, and it possesses the following physicochemical properties.

(1) Activity

It acts on naturally occurring precursors of glycinin storage protein or similar protein precursors (for example, glycinin precursors produced by microorganisms such as E. coli and the like, oat 12S globulin precursor, etc.), causing hydrolysis exactly between the C-terminal amino acid residue of the acidic subunit region, Asn, and the N-terminal amino acid residue of the basic subunit region, Gly or Asn, resulting in the maturation of the protein. In addition, it acts on peptides or denatured proteins, and hydrolyses the peptide bond on the carboxyl end of the asparagine residue, with no deamination activity (i.e., a reaction for hydrolysing the bond between Asn-$NH_2$ of DNP-Pro-Glu-Ala-Asn-$NH_2$ (see SEQ ID NO:3) or a similar peptide to liberate ammonium).

(2) Optimum pH and temperature stability

It is active in a pH range of 4.0–7.0, exhibiting maximum activity at pH 4.5–5.5. Also, with 10 minutes of thermal treatment, activity is observed up to 60° C., but the temperature for the enzyme reaction is preferably 20°–30° C.

(3) Determination of molecular weight by SDS-PAGE

It is a simple protein of molecular weight 33–46 KDa, and contains no sugar chains. More specifically, it exhibits a molecular weight of 33–33.8 KDa in soybean, 37 KDa in ginkgo nut and 46 KDa in rice.

(4) Inhibition and activation

Its activity is remarkably inhibited by 1 mM of mercury ion or copper ion, and it is also inhibited by 10 mM of zinc ion. However, with 10 mM of magnesium ion or calcium ion, or 10 mM of EDTA, there is absolutely no effect on the activity. It is completely inhibited by the SH protease inhibitors, p-chloro-mercuribenzensulfonic acid, N-ethylmaleimide and monoiodoacetic acid, at concentrations of 0.1 mM, 1.0 mM and 10 mM, respectively. The activity is also not inhibited at all by protease inhibitor peptides such as antipain, chymostatin, leupeptin, trypsin inhibitor, etc. at the final concentration of 75 mM, or by the serine protease inhibitor, phenylmethylsulfonyl fluoride (PMSF) at the final concentration of 10 mM.

In addition, it is activated by 1 mM or more of a reducing agent, for example, 2-mercaptoethanol, dithiothreitol, or the like.

Thus, the present enzyme is a thiolytic enzyme.

Methods for the measurement of the activity of the asparaginyl endoprotease according to the present invention will now be discussed.

Activity Measurement Method 1

For the measurement of the activity of the present enzyme, the product of expression of cDNA of a glycinin storage protein precursor or a similar protein precursor in a microorganism such as E. coli or the like may be used as the substrate. Here, the cDNA may be of glycinin, oat 12S globulin, glutelin, ginkgo nut 8S globulin, cottonseed gossypin, etc.

The measurement of the activity is made by addition of a sample containing the present enzyme to the substrate in an acidic buffer solution at pH 4.0–6.0 containing 0–1M of sodium chloride and 0–50 mM of 2-mercaptoethanol and reaction of the mixture at 25° C. for 3–10 hours, followed by SDS-PAGE and detection of the purified acidic and basic subunits by CBB dyeing or Western blotting. If a glycinin precursor is used, then it is necessary to add 0.2M or more of sodium chloride and 0.1M or more of 2-mercaptoethanol. The acidic buffer solution used here may be an acetate buffer solution, a sodium citrate phosphate buffer solution, etc.

Activity Measurement Method 2

The present enzyme acts on peptides or denatured proteins and hydrolyses the peptide bond on the carboxyl end of the asparagine residue, and therefore a measurement of its activity may be made using a peptide containing an asparagine residue, for example, vasoactive intestinal peptide, parathyroid hormone, neurotensin. etc. as the substrate, and may include adding a sample containing the present enzyme to the substrate in an acetate buffer solution at pH 4.0–6.0 containing 0–50 mM of 2-mercaptoethanol and reacting the mixture at 25° C.–40° C. for 10 minutes to 10 hours, and then adding an amount of acetic acid at a proportion of 1/10 thereto to stop the reaction and making an assay of the resulting peptide fragments using high performance liquid chromatography (HPLC). Here, the conditions of HPLC for assay of the resulting fragments may include adsorption of the peptide fragments onto an ODS, C8, C4 or phenyl reverse phase column, elution thereof with acetonitrile containing 0–0.1% TFA, and measurement of the UV absorption at 210–220 nm or 250–290 nm. However, in the case of enzyme samples with many contaminants, measurement of the activity by this method is difficult, and thus it is preferable to use activity measurement method 1 described above.

As described above, the asparaginyl endoprotease according to the present invention may be obtained by extracting ground seeds of an angiosperm or gymnosperm taken between the early growing stage and the ripe stage, and particularly between the early growing stage and the late growing stage, using a buffer solution at pH 4.0–6.0, dialyzing the soluble fraction, and then separating the solid and liquid. These seeds contain a large amount of storage protein, which may be separated by dialyzing a fraction which is solubilized in a buffer solution at pH 4.0–6.0, and particularly under acidic conditions at pH 4.0–5.0, in a 0–50 mM buffer solution (pH 4.0–5.0) of low ionic strength. Next, a supernatant may be obtained by centrifugal separation and used as the crude enzyme solution. If necessary, the solution may be further purified, and purification is possible to roughly the single protein level by subjecting the crude enzyme solution to, for example, hydrophobic chromatography, using Butyl-Toyopearl, Phenyl-Toyopearl, Phenyl-Sepharose, Alkyl-Sepharose, etc., and then using a Sephacryl S200, TSK-gel HW55 or the like for gel filtration, and further subjecting the solution to DEAE-Sepharose. Purification by hydrophobic chromatography is most effective.

An explanation will now be provided regarding a method for the maturation of glycinin storage protein using the novel asparaginyl endoprotease according to the present invention.

Glycinin storage protein precursors may be produced in a large quantity by using an expression vector such as pKK233-2 or the like to express the gene of the protein in a microorganism such as *E. coli*, etc., and culturing the transformed microorganism. However, in order to utilize it as a protein source, the protein must be matured.

First, the glycinin storage protein precursor obtained by culturing of the microorganism is purified by ion exchange chromatography, hydrophobic chromatography, gel filtration, etc., and upon completion thereof it is subjected to the action of the enzyme according to the present invention for maturation. For the maturation reaction, the purified glycinin storage protein precursor and 1/100 to 10-fold amounts of the present enzyme are added to a buffer solution at pH 4.0–6.0 containing 0–1M of sodium chloride and 0–50 mM of 2-mercaptoethanol, and the reaction is conducted at 25°–40° C. for 3–10 hours. If a glycinin precursor is used as the substrate, it is necessary to add 0.2M or more of sodium chloride and 0.1 mM or more of 2-mercaptoethanol to the reaction system.

Furthermore, methods for the use of the novel asparaginyl endoprotease according to the present invention may include allowing the purified enzyme to act on peptides or denatured proteins, making use of its ability to specifically cleave the peptide chains after the asparagine residues, for the mapping of such peptides. The denaturation of the protein may be effected by a method wherein the protein is heated at 60°–120° C. or is autoclaved. As reaction conditions for allowing the enzyme according to the present invention to act on a peptide or denatured protein, it is necessary to add the denatured protein and a 1/100 to 10-fold amount of the present enzyme to a buffer solution at pH 4.0–6.0 containing 0–50 mM of 2-mercaptoethanol, for the reaction at 25°–40° C. for 3–10 hours. The cleavage may be easy or difficult, depending on the amino acid sequence of the substrate used, but the cleavage always occurs after the asparagine residue. Nevertheless, in the case of NNNVEEL (SEQ ID NO:5), cleavage occurs at the carboxyl residue of the second N from the N-terminus (NNNVEEL) (SEQ ID NO:5) (See FIG. 9).

EXAMPLES

A more detailed explanation of the present invention will now be given with reference to the Examples, but the present invention is not limited to these examples.

REFERENCE 1

Asparaginyl Endoprotease Activity Measurement Method 1 cDNA lacking a leader sequence corresponding to soybean glycinin AlaB1b was inserted in-flame into expression vector pKK233-2 (product of Pharmacia), and was expressed using *E. coli* NM522 as the host. The above mentioned *E. coli* which had been cultured overnight in 10 ml of LB medium was inoculated into 1 liter of LB medium, and cultured at 23 until it reached the logarithmic growth phase (OD600 nm=0.8), after which the temperature was lowered to 13 for further culturing overnight. After completion of the culturing, the cells were collected by centrifugal separation (12,000 g, 15 minutes, 4° C.) and suspended in 100 ml of a 10 mM Tris-HCl buffer solution (pH 8.0) containing 50 mM of sodium chloride and 1 mM of EDTA.

To the suspension was added 1 ml (concentration: 10 mg/ml) of an aqueous solution of lysozyme chloride, the cells were crushed on ice using an ultrasonic crusher, and the crushed cells were removed off by centrifugal separation (11,000 g, 15 minutes, 4° C.). To the resulting supernatant was added crystalline ammonium sulfate to 30% saturation, centrifugal separation was repeated (11,000 g, 15 minutes, 4° C.) to collect a supernatant to which ammonium sulfate was further added to 70% saturation. Next, an ammonium sulfate precipitate containing Pro-AlaBlb (glycinin precursor) was obtained by centrifugal separation (11,000 g, 20 minutes, 4° C.).

The precipitate was gently dissolved in a small amount of a 35 mM potassium phosphate buffer solution (pH 7.6) which contained 0.15M of sodium chloride, after which it was dialyzed against the same type of buffer solution. Next, the dialyzed solution was adsorbed onto a Q-Sepharose column (product of Pharmacia, φ26 mm×400 mm) which had been equilibrized with the same type of buffer solution, and the non-adsorbed protein was eluted with approximately 500 ml of the same type of buffer solution, after which a linear gradient was performed with sodium chloride at a concentration of 0.15M→0.5M.

When the resulting elution fraction was analyzed by Western blotting using anti-soybean glycinin serum, the glycinin precursor was found to be eluted in the fraction collected when sodium chloride was at a concentration of 0.3–0.35M.

Ammonium sulfate was added to the glycinin precursor elution fraction to a final concentration of 1M, after which the solution was dialyzed against a 35 mM potassium phosphate buffer solution containing 1M of ammonium sulfate and 0.4M of sodium chloride. The dialyzed solution was adsorbed onto a Butyl Toyopearl 650M column (product of Toso, φ26 mm×400 mm) which had been equilibrized with the same type of buffer solution, and the non-adsorbed protein was eluted with approximately 500 ml of the same type of buffer solution, after which a linear gradient was performed with the ammonium sulfate concentration at 1M→0M to obtain a roughly single Pro-AlaBlb protein by SDS-PAGE in a 0M ammonium sulfate fraction.

The measurement of the enzyme activity was made in the following manner. The enzyme solution was added to 15 μl of a 100 mM acetate buffer solution (pH 5.0) containing 140 ng of the purified Pro-AlaBlb protein, 50 mM of mercaptoethanol and 100 mM of sodium chloride, and an enzyme reaction was conducted at 37° C. overnight. The resulting reaction solution was subjected to electrophoresis in a Laemmli system, and the antiserum to the basic subunit of glycinin was used for Western blotting. The detection was made using an immunoplot HPR kit (product of Bio-Rad Co.). The strength of the blotted band of the newly produced basic subunit (Blb) was measured for the measurement of the enzyme activity.

REFERENCE 2

Figure 6E:
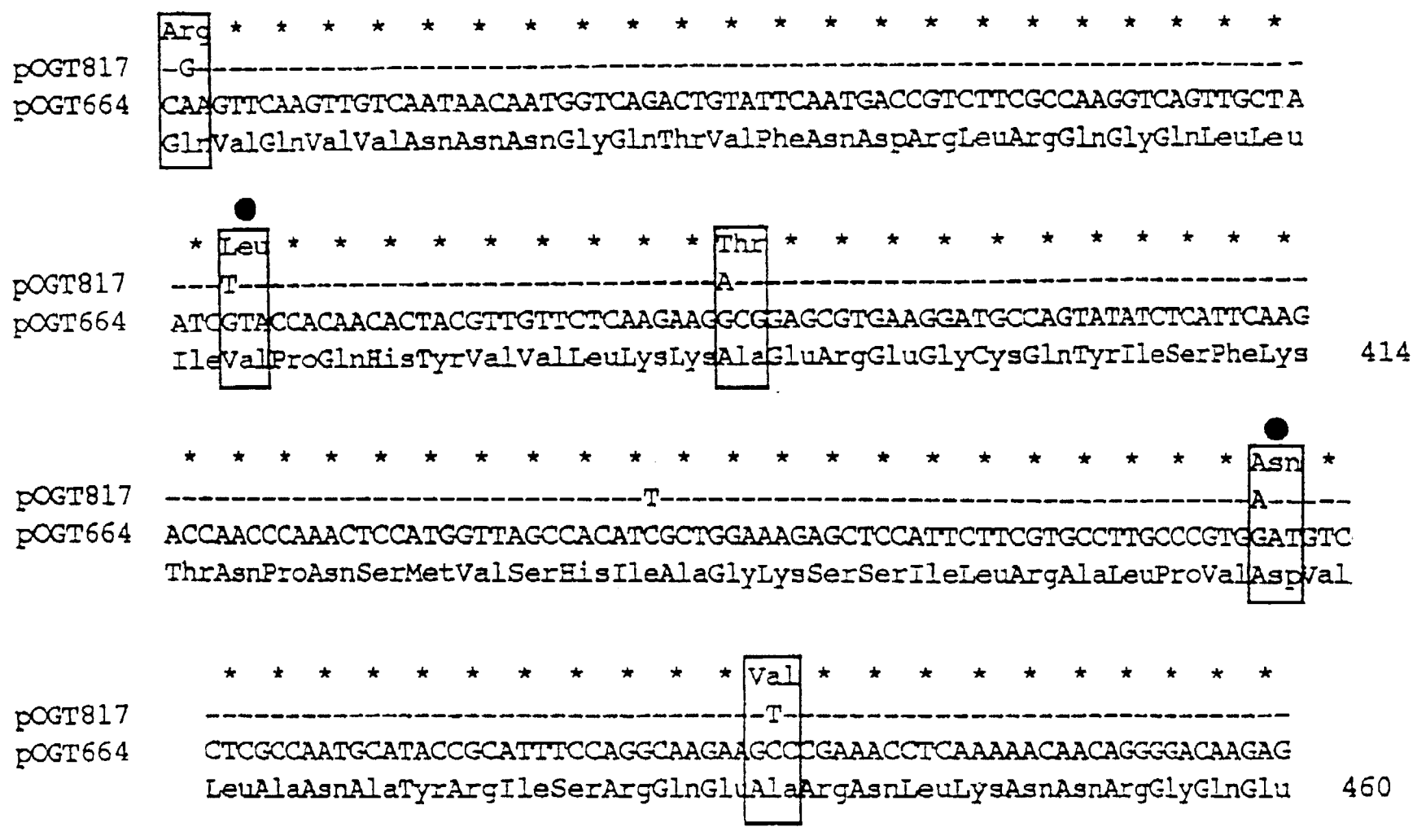
Figure 7:
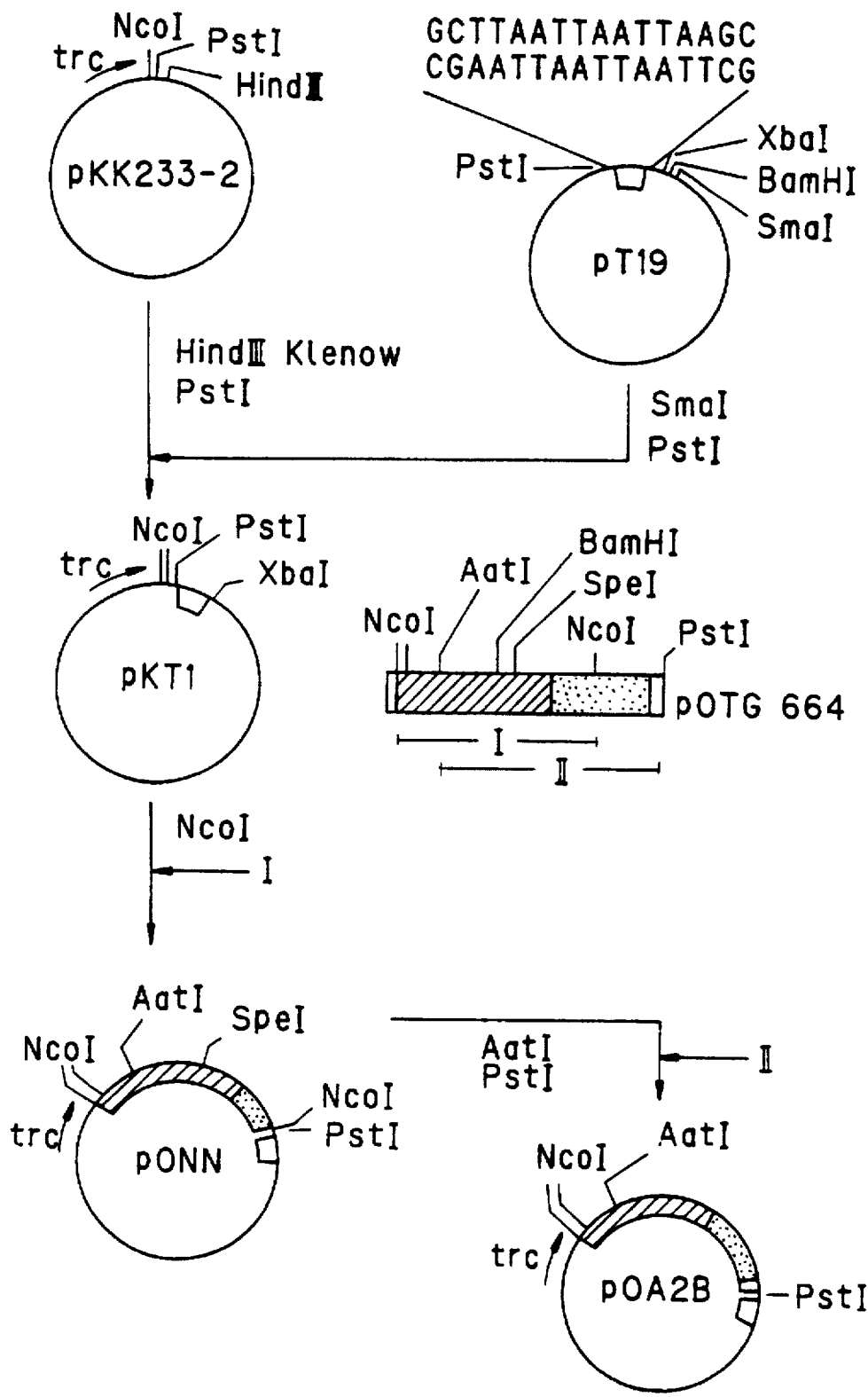
FIG. 7 is a diagram showing a method for the construction of an expression plasmid for oat 12S globulin pro-$A_2B$ in $E.\ coli$. At the top right-hand side of FIG. 7, GCTTAATTAAT-TAAGC is SEQ ID NO: 21 and CGAATTAATTAATTCG is SEQ ID NO: 22.

Asparaginyl Endoprotease Activity Measurement Method 1 cDNA corresponding to an oat 12S globulin, $A_2B$ but lacking a leader sequence thereof (see FIG. 6), was inserted in-flame into expression vector pKK233-2 (product of Pharmacia), and was expressed using E. coli JM105 as the host (see FIG. 7). The expression was induced according to the method in Reference 1, and culturing was effected at 13° C. overnight, after which the cells were subjected to ultrasonic crushing on ice in the same manner to obtain approximately 100 ml of a centrifugal supernatant. To 15 μl of the supernatant was added a 1M acetate buffer solution (pH 5.0), and then 4 μl of the enzyme solution was added thereto and an enzyme reaction was conducted at 37° C. overnight.

Next, the reaction solution was subjected to electrophoresis in a Laemmli system, and anti-oat 12S globulin serum was used for Western blotting. The detection was made using an immunoplot HPR kit (product of Bio-Rad Co.). The strength of the blotted band of the newly-resulting basic subunit ($A_2$) was measured for the measurement of the enzyme activity.

EXAMPLE 1

Harvesting of Asparaginyl Endoprotease from Ripened Soybean Seeds

Five kg of non-thermally treated and non-defatted soybean flour was gradually added to 15 liters of a 20 mM acetate buffer solution (pH 5.0) and the pH of the solution was adjusted to 5.0, after which it was gently stirred at room temperature for 2 hours. Next, the supernatant from centrifugal separation thereof (12,000 g, 10 minutes) was dialyzed against a 20 mM acetate buffer solution (pH 5.0) at 4° C. to precipitate the glycinin and other storage proteins contained in the extract, and then the solution was again subjected to centrifugal separation (12,000 g, 10 minutes) to obtain approximately 10 liters of a supernatant.

Crystalline ammonium sulfate was added to the supernatant to 40% saturation, and the solution was stirred on ice for 1 hour, and then subjected to centrifugal separation (12,000 g, 10 minutes, 4° C.) to obtain a precipitate comprising 8.4 g of protein which contained asparaginyl endoprotease. The ammonium sulfate precipitate was dissolved in 100 ml of a 10 mM acetate buffer solution (pH 5.0) containing 1M of ammonium sulfate, and was adsorbed onto Butyl Toyopearl 650M columns (φ50 mm×300 mm×2) which had been equilibrized with the same type of buffer solution, and the columns were washed with 2 liters of the same type of buffer solution, after which a linear gradient was performed while reducing the ammonium sulfate concentration at a proportion of (1M→0M)/4 liters.

Figure 2:
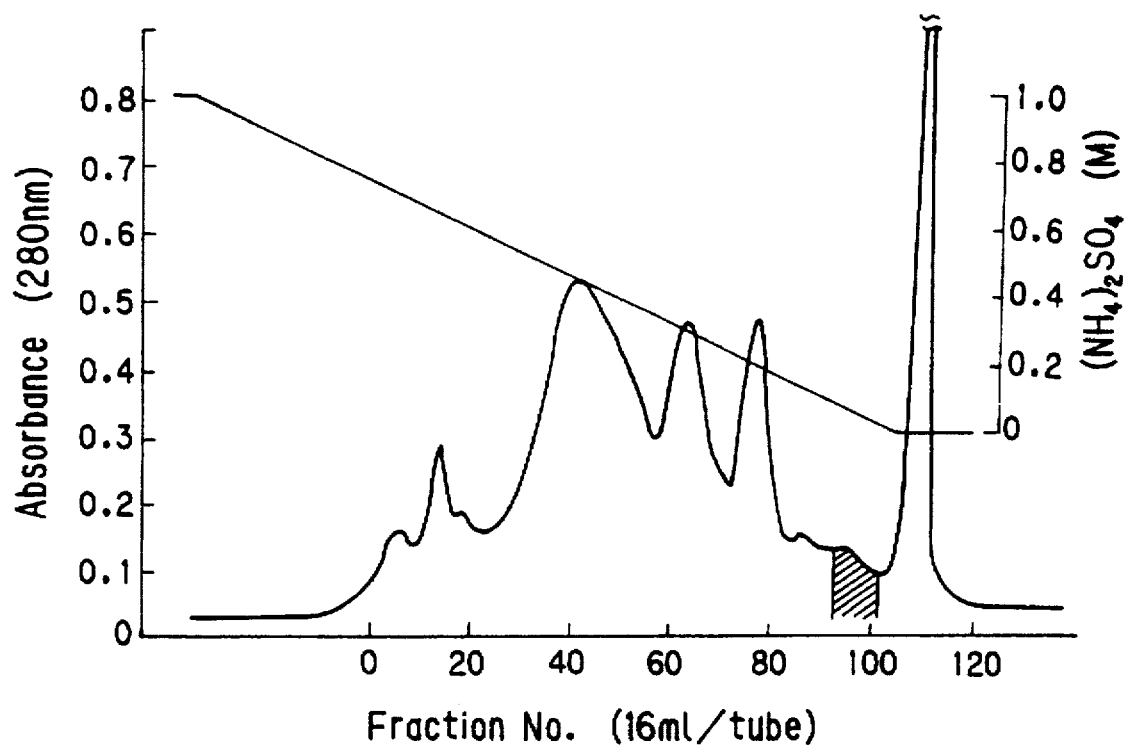
FIG. 2 is a hydrophobic chromatogram of the crude enzyme solution in Example 1. The shaded area denotes the region of strong enzyme activity.
Figure 3:
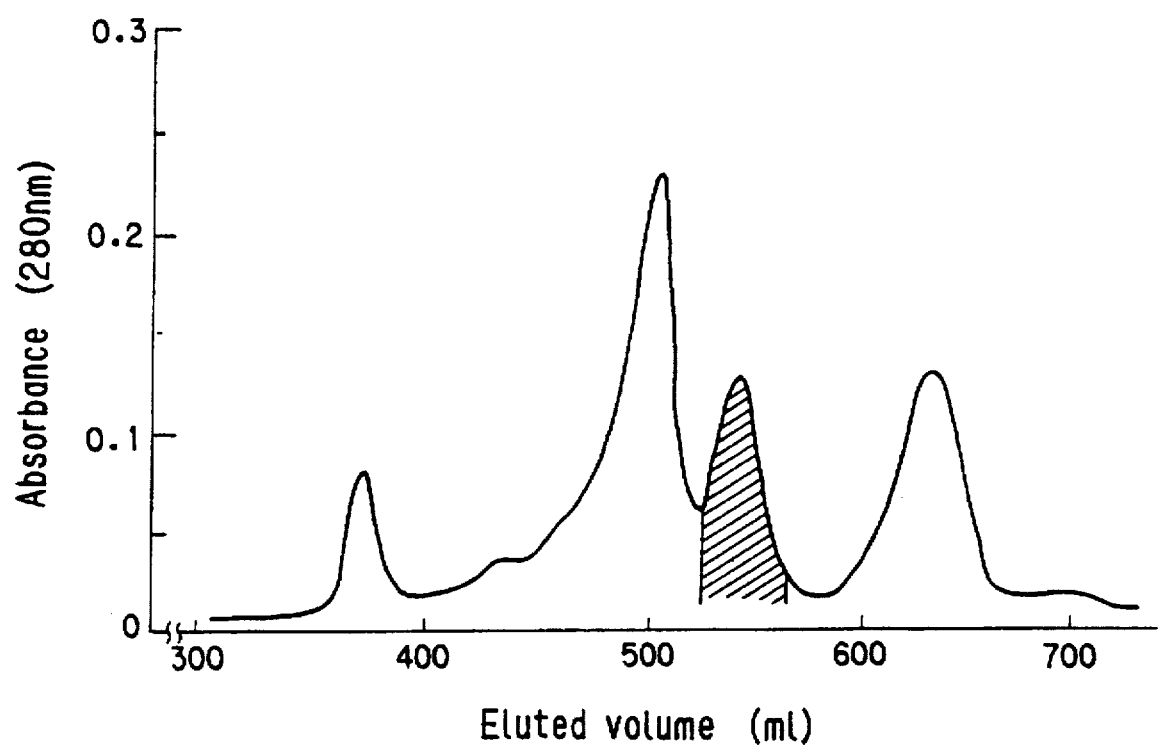
FIG. 3 is a chromatogram from gel filtration of the enzyme solution fractionated by hydrophobic chromatography in Example 1. The solution corresponding to the shaded area was collected and processed to provide the purified enzyme.

Next, when the activity of each of the fractions was measured according to the method described in Reference 1, the obtained fractions corresponding to the shaded area in FIG. 2 were found to have activity. These fractions were concentrated with a Centripret (product of Millipore Co.), and chromatography was performed using a Sephacryl S-200HR column (φ26 mm×900 mm×2). The concentrate was eluted with a 10 mM acetate buffer solution containing 0.1M of sodium chloride, and 13.4 mg of asparaginyl endoproteases A, B and C (respective isoelectric points (pI) and molecular weights (MW): pI 4.85, MW 33,800; pI 4.89, MW 33,400; pI 4.94, MW 33,000) were obtained.

EXAMPLE 2

Harvesting of Asparaginyl Endoprotease from Ginkgo Nut

Three kg of ripened ginkgo which had been adequately washed was crushed in a mortar, and then further ground to a paste using a grinder. Next, 10 liters of a 10 mM acetate buffer solution (pH 5.0) was added thereto, and extraction was effected overnight while stirring gently. Upon completion thereof, the residue was removed off by centrifugal separation (12,000 g, 20 minutes, 4° C.), and the supernatant was dialyzed three times against 50 liters of a 20 mM acetate buffer solution (pH 5.0) at 4° C. The denatured protein was removed off by centrifugal separation (12,000 g, 20 minutes, 4° C.), after which crystalline ammonium sulfate was added to 9 liters of the supernatant to achieve 30% saturation, and the mixture was stirred on ice for 1 hour and then subjected to centrifugal separation (12,000 g, 20 minutes, 4° C.) to obtain 10 liters of a supernatant.

To the supernatant was further added crystalline ammonium sulfate to 50% saturation, and the mixture was stirred on ice for 2 hours and then subjected to centrifugal separation (12,000 g, 20 minutes, 4° C.) to obtain 0.4 g of a precipitate containing asparaginyl endoprotease. Of the protein, 70 mg was dissolved in a 10 mM acetate buffer solution (pH 5.0) containing 200 ml of 1M ammonium sulfate, and adsorbed onto a Butyl Toyopearl 650M column ($\phi$50 mm×300 mm) which had been equilibrized with the same type of buffer solution, and the column was washed with 2 liters of the same type of buffer solution, after which a linear gradient was performed while reducing the concentration of ammonium sulfate at a proportion of (1M→0M)/2 liters.

Next, the activity of each fraction was measured according to the method described in Reference 1, ammonium sulfate was added to the active fraction to 80% saturation for precipitation of the enzyme, of which 3 ml was then dissolved in a 10 mM acetate solution (pH 5.0), and the solution was subjected to gel filtration on Sephacryl S-200HR columns (product of Pharmacia, $\phi$13 mm×900 mm×2) which had been equilibrized with the same type of buffer solution. The active fractions were further purified with Superose to obtain ginkgo asparaginyl endoprotease, a simple protein of molecular weight 37,000.

EXAMPLE 3

Harvesting of Asparaginyl Endoprotease from Rice

The grains used were best when fresh, since the efficiency of extraction of the enzyme was substantially lowered if they were kept at room temperature for 4–5 months after grinding. This may be due to bonding between the oil and fat components and the protein. This phenomenon was the same in the case of the other samples as well. Therefore, the rice flour used was new, finely ground rice, and not heat-dried. To 20 kg of rice flour was added in portions a 5-fold amount of a 10 mM acetate buffer solution (pH 5.0) while stirring, and the extraction was effected for 2 hours at room temperature. Next, the mixture was subjected to centrifugal separation (12,000 g, 10 minutes) to remove the residue, and a supernatant was obtained. The supernatant was sufficiently dialyzed against a 20 mM acetate buffer solution (pH 5.0) at 4° C. The resulting precipitate was removed by centrifugation to obtain a supernatant.

To the supernatant was added crystalline ammonium sulfate to 50% saturation, and the resulting precipitate (12 g of protein containing asparaginyl endoprotease) was subjected to centrifugal separation. The precipitate was then dissolved in 100 ml of a 10 mM acetate buffer solution (pH 5.0) containing 1M of ammonium sulfate, after which it was adsorbed onto Butyl Toyopearl 650M columns (50 mm×300 mm×2) which had been equilibrized with the same type of buffer solution. The column was washed with 2 liters of the same type of buffer solution, and then fractionation of the adsorbed protein was effected by the linear gradient method which reduced the concentration of ammonium sulfate at a proportion of (1M 0M)/4 liters.

Next, the activity of each of the fractions was measured according to the method described in Reference 1, for identification of the elution fractions of asparaginyl endoprotease. The protein in the fractions was precipitated with ammonium sulfate at 80% saturation, after which Sephacryl S-200 HR columns (26 mm×900 mm×2) was used for gel filtration. The method described in Reference 1 was then used to measure the enzyme activity of each of the fractionated fractions. The highly active fractions were collected, and the small amount of contaminant protein was removed by column chromatography using a DEAE-Toyopearl or other similar ion exchange resin as required, and the fractions were purified by SDS-gel electrophoresis until they displayed single bands, as shown in FIG. 8. The yield was approximately 1 mg.

EXAMPLE 4

Specific Decomposition of a Synthetic Peptide Using Asparaginyl Endoprotease

The purified enzyme described in Example 1 was added to an acetate buffer solution of pH 5.0 which contained 0.1 µg of vasoactive intestinal peptide (VIP) and 50 mM of 2-mercaptoethanol, and the mixture was reacted at 25° C. for 3 hours, after which acetic acid was added to a proportion of 1/10 to stop the enzyme reaction, and the resulting peptide fragments were analyzed by HPLC. Here, the conditions of HPLC were as follows. Column: ODS120T (product of Toso), solvent A: 0.1% TFA, solvent B: acetonitrile containing 0.1% TFA, gradient: 0.060%B/60 minutes, detection: 220 nm.

Figure 4:
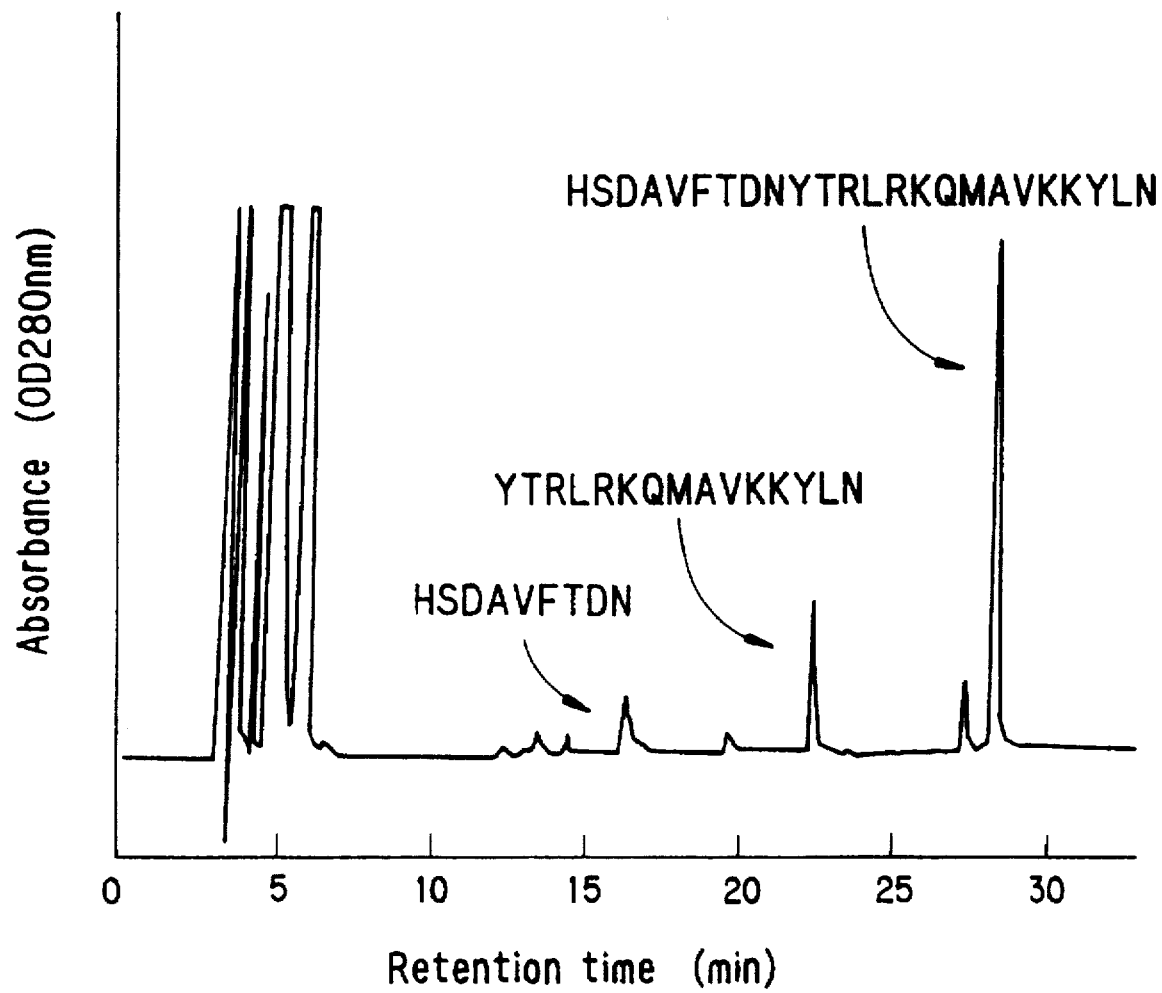
FIG. 4 is an HPLC separation graph of the peptide fragments (SEQ ID NOS. 15, 16 and 17) produced by cleavage by asparaginyl endoprotease in Example 3, wherein the primary structures of each of the resulting peptide fragments are shown next to the arrows, expressed using the single letter symbols for amino acids.

The results are shown in FIG. 4. As the figure clearly shows, the VIP was cleaved after the asparagine residue. However, there was no deaminase activity for hydrolysis of the amino group attached to the carboxyl group. This method may be applied as a method for the measurement of the enzyme activity.

EXAMPLE 5

Maturation of Glycinin Precursor Produced by *E. coli*

To 50 µg of the glycinin precursor obtained in Reference 1 above was added 4 µg of the purified enzyme obtained in Example 1, and an enzyme reaction was conducted at 25° C. for 12 hours in 50 µl of a 100 mM acetate buffer solution (pH 5.0) which contained 50 mM of mercaptoethanol and 0.5M of sodium chloride.

Figure 5:
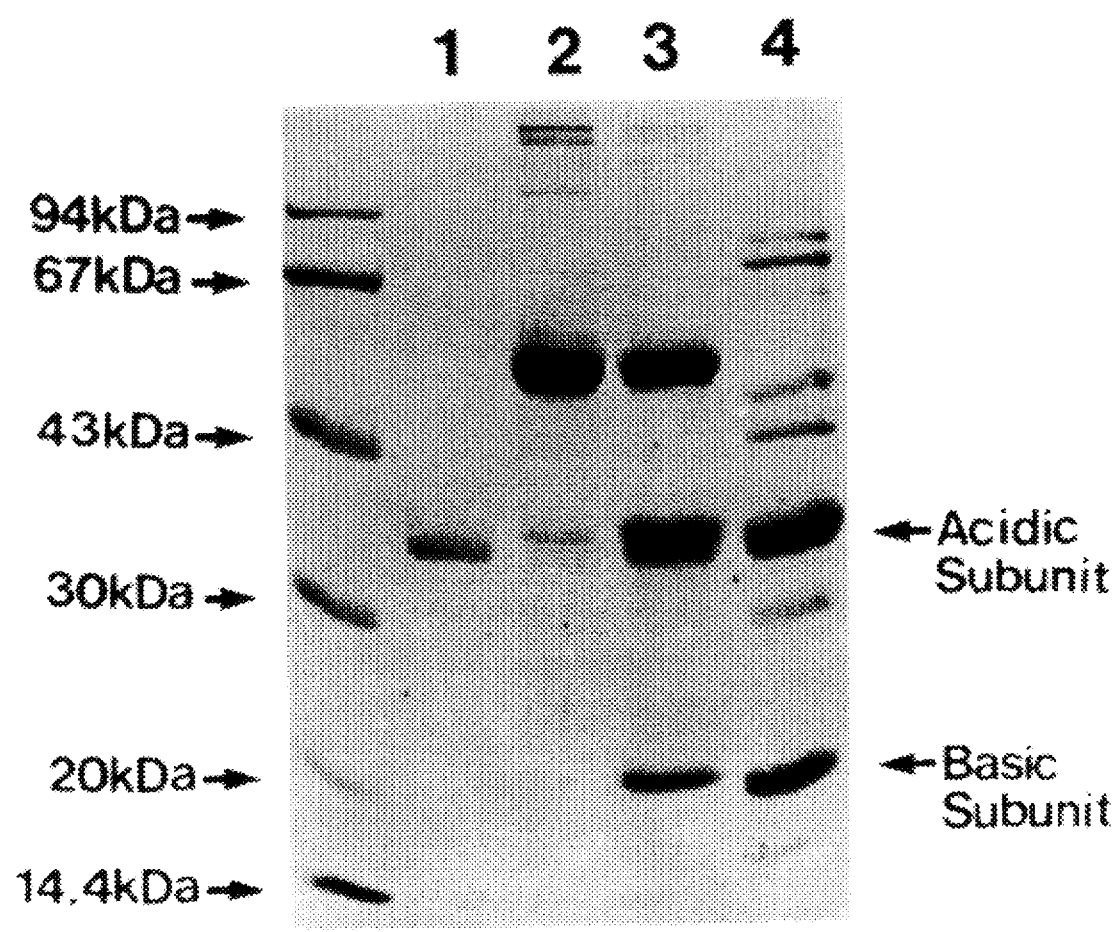
FIG. 5 is a photograph of the cleaved state of the glycinin precursor produced by $E.\ coli$, purified and subjected to enzyme action, upon its analysis by SDS-PAGE, which is described in Example 4. Lane 1 is the enzyme according to the present invention, lane 2 is the glycinin precursor used as the substrate, lane 3 is the glycinin precursor subjected to the enzyme action, and lane 4 is the cold insoluble fraction (CIF) obtained from soybean seeds. As the glycinin is concentrated in the latter fraction, it was used as the molecular weight marker.

As shown in FIG. 5, the fact that AlaBlb precursor was cleaved between its acidic and basic subunits by the present enzyme was demonstrated by SDS-PAGE. Next, in order to confirm the exactness of the cleavage site, the sequence from the N-terminal amino acid of the cleaved basic subunit (Blb) was analyzed. That is, 45 µg of the enzyme-treated AlaBlb precursor was subjected to electrophoresis, after which electroblotting was performed on a PVDF membrane (product of Millipore Co.), in a minitransplot cell (product of Bio-Rad Co.) and the N-terminal amino acid sequence of the basic subunit blotted on the PVDF membrane was analyzed using a peptide sequencer (product of ABI Co.). The results showed that the N-terminal amino acid sequence of the obtained basic subunit was identical to that of the Blb subunit obtained from soybean seeds.

On the other hand, the prepared basic subunit was isolated in the presence of 6M urea using a DEAE-Toyopearl column and then hydrolyzed with trypsin, after which it was passed through an anhydrotrypsin-HPLC column and the non-adsorbed fragment fractions were analyzed with a Pico-Tag, which revealed that the C-terminal amino acid of the acidic subunit was also identical to that from soybean seeds, or asparagine. This clearly shows that glycinin precursor is cleaved by the present enzyme exactly between the 291st amino acid, asparagine and the 292nd amino acid, glycine.

EXAMPLE 6

Maturation of Glycinin Protein Using Asparaginyl Endoprotease Present in Various Plant Seeds Five grams each of plant seeds (glycine soja, ginkgo nut, barley, corn, wheat, brown rice, tobacco, camellia, phoenix, sasanqua, pagoda, genista, wisteria, soybean, oat) from the early growing stage to the ripe stage were adequately crushed in liquid nitrogen, after which 50 ml of a 20 mM acetate buffer solution (pH 5.0) was added thereto, and the mixture was homogenized using a hiscotron while cooling on ice. Next, the supernatant obtained by removing the residue by centrifugal separation (3,000 g, 30 minutes, 4° C.) was dialyzed at 4° C. against a 20 mM acetate buffer solution (pH 5.0), the resulting precipitate was removed by further centrifugal separation (10,000 g, 30 minutes, 4° C.),and the obtained supernatant was used as a crude enzyme solution.

The glycinin protein precursor used was oat 12S globulin precursor (Pro-A$_2$B). It was expressed in *E. coli* according to the same method described in Reference 1, and to 15 µl of the purified reaction substrate (A$_2$B precursor) were added 2 µl of a 2M acetate buffer solution (pH 5.0) and 2 µl of 1M dithiothreitol, after which 11 µl of each of the above mentioned crude enzyme solutions were added thereto, enzyme reactions were conducted at 37° C. for 13 hours, and the cleaved acidic subunits were detected using Western blotting. The results, as shown in FIG. 6, confirmed that asparaginyl endoprotease was present in the various plant seeds, and also showed that it may mature glycinin protein precursors.

In addition, the following experiments were conducted in order to determine whether or not other enzymes cleave their substrates exactly after asparagine residues to produce acidic and basic subunits.

Following the method described in Example 4, peptide fragments were produced by allowing soybean asparaginyl endoprotease (5 µg) to act on oat 12S pro-A$_2$B protein (50 µg), and the N-terminal sequences of the lower molecular weight fragments were analyzed, giving the sequence Gly-Leu-Glu-Glu-Asn-Phe (SEQ ID NO:4). This perfectly matched the sequence at the N-terminal region of the basic subunit of oat 12S globulin Pro-A2B. Therefore, said enzyme derived from soybean exhibited the ability to exactly cleave protein precursors from different sources, at the same sites as those cleaved in vivo.

EXAMPLE 7

Decomposition of Synthetic Peptides Using Asparaginyl Endoprotease

Each of synthetic proteins listed below (dissolved in 0.3 µg of water or DMSO) were incubated in a 200 mM acetate buffer solution (pH 5.0) containing 50 mM of 2-mercaptoethanol at 37° C. for 6, 12 and 24 hours, after which a proportion of formic acid equal to ⅒ that of the reaction mixture was added thereto to stop the reaction. An appropriate amount of the reaction solution was analyzed by HPLC. The results are shown in FIG. 7. C$_4$–C$_{18}$ reverse phase columns were used, choosing an appropriate column depending on the length of the peptide.

Synthetic peptides (cleavage site denoted by)

(1) NH$_2$-NNVEEL (uncleavable)

(2) NH$_2$-NN↑NVEEL (SEQ ID NO:5) (cleavable, but difficult)

(3) NH$_2$-NN↑N↑NVEEL (SEQ ID NO:6) (cleavable at 2 sites, one easily)

(4) NH$_2$-NNN↑SEEL (SEQ ID NO:7) (cleavable, but difficult)

(5) NH$_2$-NNN↑EVEL (SEQ ID NO:8) (easily cleaved)

(6) NH$_2$-SESEN↑GLEET (SEQ ID NO:9) (easily cleaved)

(7) NH$_2$-FNNVEEL (SEQ ID NO:10) (difficult to cleave)

(8) NH$_2$-NN↑NLEEL (SEQ ID NO:11) (cleavable, but difficult)

(9) NH$_2$-NNN↑ELEL (SEQ ID NO:12) (easily cleavable)

(10) NH$_2$-NN↑NIEEL (SEQ ID NO:13) (cleavable; but difficult)

(11) NH$_2$-NNN↑EIEL (SEQ ID NO:14) (very much cleavable)

(12) Boc-N-OPhNO$_2$ (uncleavable)

(13) DNP-PEAN-NH$_2$ (SEQ ID NO:3) (uncleavable)

(14) Z-AAN-NH$_2$ (uncleavable)

Thus, when a hydrophobic amino acid such as V, I or L follows N, the chain is not cleaved by the present enzyme. As a result, in the case of (1), NNVEEL (SEQ ID NO:19) can occur, but since the present enzyme has no amino peptidase activity, (1) is not cleaved. Also, (2) is cleaved at the site of the arrow, but (3) is more easily cleaved. If V is replaced by a non-hydrophobic, comparatively small molecular sized amino acid such as S, G, etc., the peptide becomes cleavable, but a more efficient cleavage results, if N is followed by a non-hydrophobic amino acid residue which is immediately followed by a hydrophobic amino acid residue; for example, in a cleavage environment such as - - - NGV - - - , the Peptide is easily cleaved after N. Also, provided that one or more other amino acids are present upstream from the N at the cleavage site (XNYφ - - - , where X is an amino acid residue different from φ, Y is different from φ and is an amino acid of comparatively small molecular size such as A, S, T, P, G, etc., and φ is a hydrophobic amino acid residue), the cleavage becomes easier if 3–4 or more amino acid residues are present. FIG. 8 shows an example of the separation of a peptide by cleavage in a case in which the present enzyme was allowed to act on the peptide NH$_2$-NNNVEEL-COOH (SEQ ID NO:5). From analysis of the amino acid sequence of the collected peptide fragments, it was clear that cleavage occurred at the site of the arrow in NN↑NVEEL (SEQ ID NO:5).

As described above, according to the present invention a novel asparaginyl endoprotease obtained from the seeds of angiosperms or gymnosperms, and a method for the production thereof, are provided. Incidentally, in order to utilize the glycinin storage proteins contained in plant seeds, gene recombinant techniques are being used in an attempt at their mass production, but the proteins obtained by these methods are precursors. For their practical use as protein sources, their maturation is necessary. The enzyme according to the present invention may be allowed to act on said glycinin storage protein precursors for their maturation, and therefore the present enzyme is very useful for the utilization of glycinin storage proteins obtained from plant seeds.

Furthermore, by using the present enzyme to cleave proteins at the carboxyl end of asparagine residues, a structural analysis of the cleavage site is possible. As a result, by using the present enzyme, an amount of the peptide required for an analysis of its primary structure may be easily produced.

What is claimed is:

1. A method for producing asparaginyl endoprotease which comprises:

extracting ground seeds of soybean, ginkgo or rice, said seeds being collected between an early growing stage and ripening, with a first buffer solution having a pH 4.0 to 6.0 to obtain a soluble fraction, dialyzing said soluble fraction against a second buffer solution to form a precipitate, subjecting the dialyzed soluble fraction to a centrifugation to obtain a supernatant, subjecting said supernatant to ammonium sulfate fractionation to obtain a solid containing the asparaginyl endoprotease, dissolving the solid in a third buffer solution and subjecting the resultant solution containing the asparaginyl endoprotease to hydrophobic chromatography and then to gel filtration and recovering the asparaginyl endoprotease, wherein the asparaginyl endoprotease possesses following properties:

(a) when contacted with proglycinin, cleavage of glycinin occurs between the C-terminal amino acid Asn of the acidic subunit region and the N-terminal amino acid Gly or Asn of the basic subunit region, (b) is active at a pH of 4.0 to 7.0, (c) is a cysteine protease, (d) has a molecular weight of 33 KDa to 46 KDa, and does not have sugar chains, (e) is not absorbed onto a concanavalin A-Sepharose column, (f) reacts with peptides or denatured proteins, and hydrolyses the peptide bond on the carboxyl end of an asparagine residue, but does not react with peptides selected from the group consisting of Boc-Asn-nitrophenyl, DNP-Pro-Glu-Ala-Asn-NH$_2$ (SEQ ID NO: 3) and Z-Ala-Ala-Asn-NH$_2$, and (g) is synthesized substantially at an early stage of seed embryogenesis and is degraded in early imbibition such that both the asparaginyl endoprotease and the proglycinin are completely consumed after 12 hour imbibition in an immunoblotting assay.

2. The method of claim 1, wherein the second buffer solution has a pH of 4.0 to 5.0.

3. The method of claim 1, wherein the seeds are soybean seeds.

4. The method of claim 3, wherein the first and second buffer solutions are 20 mM acetate buffer solutions having a pH of 5.

5. The method of claim 4, wherein the centrifugation is carried out at 12,000g for 10 minutes.

6. The method of claim 5, wherein the dialyzing is conducted at 4° C.

7. The method of claim 1, wherein the seeds are ginkgo seeds.

8. The method of claim 7, wherein the first and third buffer solutions are 10 mM acetate solutions having a pH of 5.0, the centrifugation is carried out at 12,000g for 20 minutes at 4° C. and the dialyzing is conducted at 4° C. against a 20 mM acetate buffer solution having a pH of 5.0.

9. The method of claim 1, wherein the seeds are rice seeds.

10. The method of claim 9, wherein the first and third buffer solutions are 10 mM acetate solutions having a pH of 5.0 and the dialyzing is conducted at 4° C. against a 20 mM acetate buffer solution.

* * * * *